(12) United States Patent
Ruan et al.

(10) Patent No.: US 11,213,206 B2
(45) Date of Patent: Jan. 4, 2022

(54) NON-INVASIVE MEASUREMENT SYSTEMS WITH SINGLE-PHOTON COUNTING CAMERA

(71) Applicant: HI LLC, Los Angeles, CA (US)

(72) Inventors: Haowen Ruan, Pasadena, CA (US); Haojiang Zhou, Los Angeles, CA (US); Yuecheng Shen, Guangdong (CN); Roarke Horstmeyer, Durham, NC (US)

(73) Assignee: HI LLC, Los Angeles, CA (US)

( * ) Notice: Subject to any disclaimer, the term of this patent is extended or adjusted under 35 U.S.C. 154(b) by 443 days.

(21) Appl. No.: 16/432,793

(22) Filed: Jun. 5, 2019

(65) Prior Publication Data

US 2020/0022578 A1    Jan. 23, 2020

Related U.S. Application Data

(60) Provisional application No. 62/699,656, filed on Jul. 17, 2018, provisional application No. 62/772,584, filed on Nov. 28, 2018.

(51) Int. Cl.
*A61B 5/00* (2006.01)
*H04N 5/30* (2006.01)
(Continued)

(52) U.S. Cl.
CPC .......... *A61B 5/0042* (2013.01); *A61B 5/0075* (2013.01); *A61B 5/6803* (2013.01);
(Continued)

(58) Field of Classification Search
CPC ............ A61B 2576/026; A61B 5/0042; A61B 5/0035; A61B 5/0066; A61B 5/4064;
(Continued)

(56) References Cited

U.S. PATENT DOCUMENTS

| 4,018,534 A | 4/1977 | Thorn et al. |
| 4,207,892 A | 6/1980 | Binder |

(Continued)

FOREIGN PATENT DOCUMENTS

| CN | 200950235 | 9/2007 |
| CN | 107865635 | 4/2018 |

(Continued)

OTHER PUBLICATIONS

"emojipedia.org", https://emojipedia.org (accessed May 27, 2021).
(Continued)

*Primary Examiner* — Que Tan Le
(74) *Attorney, Agent, or Firm* — ALG Intellectual Property, LLC

(57) ABSTRACT

An exemplary non-invasive measurement system includes a single-photon counting camera and a processor. The single-photon counting camera includes an array of SPAD detectors configured to detect, during a sequence of gated time intervals, coherent continuous light that exits a body after the light enters and scatters within the body, and output a plurality of electronic signals representative of the detected light. The processor is configured to generate, based on the electronic signals, a sequence of speckle pattern image frames corresponding to the gated time intervals. Other exemplary non-invasive measurement systems are also described.

20 Claims, 14 Drawing Sheets

(51) Int. Cl.
  *G01J 1/44* (2006.01)
  *G01J 1/04* (2006.01)
(52) U.S. Cl.
  CPC ............ *G01J 1/0425* (2013.01); *G01J 1/44* (2013.01); *H04N 5/30* (2013.01); *A61B 2562/0238* (2013.01); *A61B 2576/026* (2013.01); *G01J 2001/442* (2013.01); *G01J 2001/448* (2013.01); *G01J 2001/4466* (2013.01)
(58) Field of Classification Search
  CPC ........... A61B 5/6803; G01N 2021/479; G01N 21/49; G01N 21/4795; H04N 5/30; G01J 2001/442; G01J 2001/4466; G01J 2001/448
  USPC ........................ 250/208.1, 214 R, 221, 559.4
  See application file for complete search history.

(56) References Cited

U.S. PATENT DOCUMENTS

| | | | |
|---|---|---|---|
| 4,281,645 A | 8/1981 | Jobsis | |
| 4,321,930 A | 3/1982 | Jobsis | |
| 4,515,165 A | 5/1985 | Carroll | |
| 4,655,225 A | 4/1987 | Dahne et al. | |
| 4,928,248 A | 5/1990 | Takahashi et al. | |
| 4,963,727 A | 10/1990 | Cova | |
| 4,995,044 A | 2/1991 | Blazo | |
| 5,088,493 A | 2/1992 | Giannini | |
| 5,090,415 A | 2/1992 | Yamashita | |
| 5,309,458 A | 5/1994 | Carl | |
| 5,386,827 A | 2/1995 | Chance et al. | |
| 5,528,365 A | 6/1996 | Gonatas et al. | |
| 5,625,458 A | 4/1997 | Alfano et al. | |
| 5,761,230 A | 6/1998 | Oono et al. | |
| 5,853,370 A | 12/1998 | Chance et al. | |
| 5,895,984 A | 4/1999 | Renz | |
| 5,929,982 A | 7/1999 | Anderson | |
| 5,983,120 A | 11/1999 | Groner et al. | |
| 5,987,045 A | 11/1999 | Albares et al. | |
| 6,163,715 A | 12/2000 | Larsen et al. | |
| 6,240,309 B1 | 5/2001 | Yamashita et al. | |
| 6,384,663 B2 | 5/2002 | Cova et al. | |
| 6,541,752 B2 | 4/2003 | Zappa et al. | |
| 6,640,133 B2 | 10/2003 | Yamashita | |
| 6,683,294 B1 | 1/2004 | Herbert et al. | |
| 6,748,254 B2 | 6/2004 | O'Neil | |
| 6,992,772 B2 | 1/2006 | Block | |
| 7,095,491 B2 | 8/2006 | Forstner et al. | |
| 7,231,243 B2 * | 6/2007 | Tearney ............. | A61B 1/00082 600/407 |
| 7,356,365 B2 | 4/2008 | Schurman | |
| 7,507,596 B2 | 3/2009 | Yaung et al. | |
| 7,547,872 B2 | 6/2009 | Niclass et al. | |
| 7,613,504 B2 | 11/2009 | Rowe | |
| 7,667,400 B1 | 2/2010 | Goushcha | |
| 7,705,284 B2 | 4/2010 | Inoue et al. | |
| 7,714,292 B2 | 5/2010 | Agarwal et al. | |
| 7,774,047 B2 | 8/2010 | Yamashita et al. | |
| 7,899,506 B2 | 3/2011 | Xu et al. | |
| 8,026,471 B2 | 9/2011 | Itzler | |
| 8,078,250 B2 | 12/2011 | Chen et al. | |
| 8,082,015 B2 | 12/2011 | Yodh et al. | |
| 8,115,170 B2 | 2/2012 | Stellari et al. | |
| 8,168,934 B2 | 5/2012 | Niclass et al. | |
| 8,352,012 B2 | 1/2013 | Besio | |
| 8,633,431 B2 | 1/2014 | Kim | |
| 8,637,875 B2 | 1/2014 | Finkelstein et al. | |
| 8,754,378 B2 | 6/2014 | Prescher et al. | |
| 8,817,257 B2 | 8/2014 | Herve | |
| 8,937,509 B2 | 1/2015 | Xu et al. | |
| 8,986,207 B2 | 3/2015 | Li | |
| 9,012,860 B2 | 4/2015 | Nyman et al. | |
| 9,041,136 B2 | 5/2015 | Chia | |
| 9,058,081 B2 | 6/2015 | Baxter | |
| 9,076,707 B2 | 7/2015 | Harmon | |
| 9,101,279 B2 | 8/2015 | Ritchey et al. | |
| 9,131,861 B2 | 9/2015 | Ince et al. | |
| 9,157,858 B2 | 10/2015 | Claps | |
| 9,160,949 B2 | 10/2015 | Zhang et al. | |
| 9,176,241 B2 | 11/2015 | Frach | |
| 9,178,100 B2 | 11/2015 | Webster et al. | |
| 9,190,552 B2 | 11/2015 | Brunel et al. | |
| 9,201,138 B2 | 12/2015 | Eisele et al. | |
| 9,209,320 B1 | 12/2015 | Webster | |
| 9,257,523 B2 | 2/2016 | Schneider et al. | |
| 9,257,589 B2 | 2/2016 | Niclass et al. | |
| 9,299,732 B2 | 3/2016 | Webster et al. | |
| 9,299,873 B2 | 3/2016 | Mazzillo et al. | |
| 9,312,401 B2 | 4/2016 | Webster | |
| 9,316,735 B2 | 4/2016 | Baxter | |
| 9,331,116 B2 | 5/2016 | Webster | |
| 9,368,487 B1 | 6/2016 | Su et al. | |
| 9,401,448 B2 | 7/2016 | Bienfang et al. | |
| 9,407,796 B2 | 8/2016 | Dinten et al. | |
| 9,419,635 B2 | 8/2016 | Kumar et al. | |
| 9,431,439 B2 | 8/2016 | Soga et al. | |
| 9,442,201 B2 | 9/2016 | Schmand et al. | |
| 9,449,377 B2 | 9/2016 | Sarkar et al. | |
| 9,450,007 B1 | 9/2016 | Motta et al. | |
| 9,466,631 B2 | 10/2016 | Fallica et al. | |
| 9,476,979 B2 | 10/2016 | Drader et al. | |
| 9,478,579 B2 | 10/2016 | Dai et al. | |
| 9,529,079 B1 | 12/2016 | Droz | |
| 9,535,157 B2 | 1/2017 | Caley et al. | |
| 9,574,936 B2 | 2/2017 | Heinonen | |
| 9,625,580 B2 | 4/2017 | Kotelnikov et al. | |
| 9,627,569 B2 | 4/2017 | Harmon | |
| 9,639,063 B2 | 5/2017 | Dutton et al. | |
| 9,640,704 B2 | 5/2017 | Frey et al. | |
| 9,658,158 B2 | 5/2017 | Renna et al. | |
| 9,659,980 B2 | 5/2017 | McGarvey et al. | |
| 9,671,284 B1 | 6/2017 | Dandin | |
| 9,681,844 B2 | 6/2017 | Xu et al. | |
| 9,685,576 B2 | 6/2017 | Webster | |
| 9,702,758 B2 | 7/2017 | Nouri | |
| 9,728,659 B2 | 8/2017 | Hirigoyen et al. | |
| 9,741,879 B2 | 8/2017 | Frey et al. | |
| 9,753,351 B2 | 9/2017 | Eldada | |
| 9,767,246 B2 | 9/2017 | Dolinsky et al. | |
| 9,768,211 B2 | 9/2017 | Harmon | |
| 9,773,930 B2 | 9/2017 | Motta et al. | |
| 9,804,092 B2 | 10/2017 | Zeng et al. | |
| 9,812,438 B2 | 11/2017 | Schneider et al. | |
| 9,831,283 B2 | 11/2017 | Shepard et al. | |
| 9,851,302 B2 | 12/2017 | Mattioli Della Rocca et al. | |
| 9,867,250 B1 | 1/2018 | Powers et al. | |
| 9,869,753 B2 | 1/2018 | Eldada | |
| 9,881,963 B1 | 1/2018 | Chen et al. | |
| 9,882,003 B1 | 1/2018 | Aharoni | |
| 9,886,095 B2 | 2/2018 | Pothier | |
| 9,899,544 B1 | 2/2018 | Mazzillo et al. | |
| 9,899,557 B2 | 2/2018 | Muscara' et al. | |
| 9,939,316 B2 | 4/2018 | Scott et al. | |
| 9,939,536 B2 | 4/2018 | O'Neill et al. | |
| 9,946,344 B2 | 4/2018 | Ayaz et al. | |
| D817,553 S | 5/2018 | Aaskov et al. | |
| 9,983,670 B2 | 5/2018 | Coleman | |
| 10,016,137 B1 | 7/2018 | Yang et al. | |
| D825,112 S | 8/2018 | Saez | |
| 10,056,415 B2 | 8/2018 | Na et al. | |
| 10,103,513 B1 | 10/2018 | Zhang et al. | |
| 10,141,458 B2 | 11/2018 | Zhang et al. | |
| 10,157,954 B2 | 12/2018 | Na et al. | |
| 10,158,038 B1 | 12/2018 | Do Valle et al. | |
| 10,219,700 B1 | 3/2019 | Yang et al. | |
| 10,256,264 B2 | 4/2019 | Na et al. | |
| 10,340,408 B1 | 7/2019 | Katnani | |
| 10,424,683 B1 | 9/2019 | Do Valle | |
| 10,483,125 B2 | 11/2019 | Inoue | |
| 10,515,993 B2 | 12/2019 | Field et al. | |
| 10,533,893 B2 | 1/2020 | Leonardo | |
| 10,558,171 B2 | 2/2020 | Kondo | |

(56) References Cited

U.S. PATENT DOCUMENTS

| | | |
|---|---|---|
| 10,594,306 B2 | 3/2020 | Dandin |
| 10,627,460 B2 | 4/2020 | Alford et al. |
| 10,697,829 B2 | 6/2020 | Delic |
| 10,772,561 B2 | 9/2020 | Donaldson |
| 10,809,796 B2 | 10/2020 | Armstrong-Muntner |
| 10,825,847 B2 | 11/2020 | Furukawa |
| 10,912,504 B2 | 2/2021 | Nakaji |
| 10,976,386 B2 | 4/2021 | Alford |
| 10,983,177 B2 | 4/2021 | Jiménez-Martínez |
| 10,996,293 B2 | 5/2021 | Mohseni |
| 11,006,876 B2 | 5/2021 | Johnson |
| 11,006,878 B2 | 5/2021 | Johnson |
| 2004/0057478 A1 | 3/2004 | Saito |
| 2004/0078216 A1 | 4/2004 | Toto |
| 2004/0160996 A1 | 8/2004 | Giorgi et al. |
| 2005/0061986 A1 | 3/2005 | Kardynal et al. |
| 2006/0197452 A1 | 9/2006 | Zhang |
| 2007/0038116 A1 | 2/2007 | Yamanaka |
| 2007/0083097 A1 | 4/2007 | Fujiwara |
| 2008/0021341 A1 | 1/2008 | Harris et al. |
| 2009/0012402 A1 | 1/2009 | Mintz |
| 2009/0163775 A1 | 6/2009 | Barrett |
| 2009/0313048 A1 | 12/2009 | Kahn et al. |
| 2010/0210952 A1 | 8/2010 | Taira et al. |
| 2011/0208675 A1 | 8/2011 | Shoureshi et al. |
| 2012/0029304 A1 | 2/2012 | Medina et al. |
| 2012/0101838 A1 | 4/2012 | Lingard et al. |
| 2013/0030267 A1 | 1/2013 | Lisogurski |
| 2013/0032713 A1 | 2/2013 | Barbi et al. |
| 2013/0144644 A1 | 6/2013 | Simpson |
| 2013/0221221 A1 | 8/2013 | Bouzid et al. |
| 2013/0342835 A1 | 12/2013 | Blacksberg |
| 2014/0027607 A1 | 1/2014 | Mordarski et al. |
| 2014/0066783 A1 | 3/2014 | Kiani |
| 2014/0185643 A1 | 7/2014 | McComb et al. |
| 2014/0191115 A1 | 7/2014 | Webster et al. |
| 2014/0211194 A1 | 7/2014 | Pacala et al. |
| 2014/0275891 A1 | 9/2014 | Muehlemann et al. |
| 2014/0289001 A1 | 9/2014 | Shelton |
| 2014/0291481 A1 | 10/2014 | Zhang et al. |
| 2015/0041625 A1 | 2/2015 | Dutton |
| 2015/0041627 A1 | 2/2015 | Webster |
| 2015/0054111 A1 | 2/2015 | Niclass et al. |
| 2015/0057511 A1 | 2/2015 | Basu |
| 2015/0077279 A1 | 3/2015 | Song |
| 2015/0094552 A1 | 4/2015 | Golda |
| 2015/0150505 A1 | 6/2015 | Kaskoun et al. |
| 2015/0182136 A1 | 7/2015 | Durduran et al. |
| 2015/0192677 A1 | 7/2015 | Yu et al. |
| 2015/0200222 A1 | 7/2015 | Webster |
| 2015/0293224 A1 | 10/2015 | Eldada et al. |
| 2015/0327777 A1 | 11/2015 | Kostic et al. |
| 2015/0333095 A1 | 11/2015 | Fallica et al. |
| 2015/0364635 A1 | 12/2015 | Bodlovic et al. |
| 2016/0049765 A1 | 2/2016 | Eldada |
| 2016/0099371 A1 | 4/2016 | Webster |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | McGarvey et al. |
| 2016/0218236 A1 | 7/2016 | Dhulla et al. |
| 2016/0247301 A1 | 8/2016 | Fang |
| 2016/0278715 A1 | 9/2016 | Yu et al. |
| 2016/0287107 A1 | 10/2016 | Szabados |
| 2016/0341656 A1 | 11/2016 | Liu et al. |
| 2016/0345880 A1 | 12/2016 | Nakaji et al. |
| 2016/0356718 A1 | 12/2016 | Yoon et al. |
| 2016/0357260 A1 | 12/2016 | Raynor et al. |
| 2017/0030769 A1 | 2/2017 | Clemens et al. |
| 2017/0047372 A1 | 2/2017 | McGarvey et al. |
| 2017/0052065 A1 | 2/2017 | Sharma et al. |
| 2017/0118423 A1 | 4/2017 | Zhou et al. |
| 2017/0124713 A1 | 5/2017 | Jurgenson et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0176579 A1 | 6/2017 | Niclass et al. |
| 2017/0176596 A1 | 6/2017 | Shpunt et al. |
| 2017/0179173 A1 | 6/2017 | Mandai et al. |
| 2017/0186798 A1 | 6/2017 | Yang et al. |
| 2017/0202518 A1 | 7/2017 | Furman et al. |
| 2017/0265822 A1 | 9/2017 | Du |
| 2017/0276545 A1 | 9/2017 | Henriksson |
| 2017/0281086 A1 | 10/2017 | Donaldson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0363467 A1 | 12/2017 | Clemens et al. |
| 2018/0003821 A1 | 1/2018 | Imai |
| 2018/0014741 A1 | 1/2018 | Chou |
| 2018/0019268 A1 | 1/2018 | Zhang et al. |
| 2018/0020960 A1 | 1/2018 | Sarussi |
| 2018/0026147 A1 | 1/2018 | Zhang et al. |
| 2018/0027196 A1 | 1/2018 | Yang et al. |
| 2018/0033895 A1 | 2/2018 | Mazzillo et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0069043 A1 | 3/2018 | Pan et al. |
| 2018/0070830 A1 | 3/2018 | Sutin et al. |
| 2018/0070831 A1 | 3/2018 | Sutin et al. |
| 2018/0081061 A1 | 3/2018 | Mandai et al. |
| 2018/0089531 A1 | 3/2018 | Geva et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0102442 A1 | 4/2018 | Wang et al. |
| 2018/0103528 A1 | 4/2018 | Moore |
| 2018/0103861 A1 | 4/2018 | Sutin et al. |
| 2018/0156660 A1 | 6/2018 | Turgeon |
| 2018/0167606 A1 | 6/2018 | Cazaux et al. |
| 2018/0175230 A1 | 6/2018 | Droz et al. |
| 2018/0185667 A1 | 7/2018 | Huang |
| 2018/0217261 A1 | 8/2018 | Wang |
| 2018/0296094 A1 | 10/2018 | Nakamura |
| 2018/0366342 A1 | 12/2018 | Inoue et al. |
| 2019/0006399 A1 | 1/2019 | Otake et al. |
| 2019/0026849 A1 | 1/2019 | Demeyer |
| 2019/0088697 A1 | 3/2019 | Furukawa et al. |
| 2019/0091483 A1 | 3/2019 | Deckert |
| 2019/0113385 A1 | 4/2019 | Fukuchi |
| 2019/0167211 A1 | 6/2019 | Everman et al. |
| 2019/0175068 A1 | 6/2019 | Everdell |
| 2019/0200888 A1 | 7/2019 | Poltorak |
| 2019/0261869 A1 | 8/2019 | Franceschini |
| 2019/0298158 A1 | 10/2019 | Dhaliwal |
| 2019/0343395 A1 | 11/2019 | Cussac |
| 2019/0355773 A1 | 11/2019 | Field et al. |
| 2019/0355861 A1 | 11/2019 | Katnani |
| 2019/0363210 A1 | 11/2019 | Do Valle |
| 2019/0378869 A1 | 12/2019 | Field et al. |
| 2019/0388018 A1 | 12/2019 | Horstmeyer |
| 2019/0391213 A1 | 12/2019 | Alford |
| 2020/0056263 A1 | 2/2020 | Bhattacharyya |
| 2020/0057115 A1 | 2/2020 | Jiménez-Martínez |
| 2020/0057116 A1 | 2/2020 | Zorzos et al. |
| 2020/0088811 A1 | 3/2020 | Mohseni |
| 2020/0109481 A1 | 4/2020 | Sobek |
| 2020/0123416 A1 | 4/2020 | Bhattacharyya |
| 2020/0182692 A1 | 6/2020 | Lilic |
| 2020/0191883 A1 | 6/2020 | Bhattacharyya |
| 2020/0196932 A1 | 6/2020 | Johnson |
| 2020/0241094 A1 | 7/2020 | Alford |
| 2020/0256929 A1 | 8/2020 | Ledbetter et al. |
| 2020/0309873 A1 | 10/2020 | Ledbetter et al. |
| 2020/0315510 A1 | 10/2020 | Johnson |
| 2020/0334559 A1 | 10/2020 | Anderson |
| 2020/0337624 A1 | 10/2020 | Johnson |
| 2020/0341081 A1 | 10/2020 | Mohseni et al. |
| 2020/0348368 A1 | 11/2020 | Garber et al. |
| 2020/0381128 A1 | 12/2020 | Pratt |
| 2020/0390358 A1 | 12/2020 | Johnson |
| 2020/0393902 A1 | 12/2020 | Mann et al. |
| 2020/0400763 A1 | 12/2020 | Pratt |

(56) References Cited

U.S. PATENT DOCUMENTS

| | | |
|---|---|---|
| 2021/0015385 A1 | 1/2021 | Katnani |
| 2021/0011094 A1 | 2/2021 | Bednarke |
| 2021/0041512 A1 | 2/2021 | Pratt |
| 2021/0063510 A1 | 3/2021 | Ledbetter |
| 2021/0013974 A1 | 5/2021 | Seidman |
| 2021/0139742 A1 | 5/2021 | Seidman |

FOREIGN PATENT DOCUMENTS

| | | |
|---|---|---|
| EP | 0656536 | 4/2004 |
| EP | 3487072 | 5/2019 |
| WO | 8804034 | 6/1988 |
| WO | 1999053577 | 10/1999 |
| WO | 2008144831 | 12/2008 |
| WO | 2015052523 | 4/2015 |
| WO | 2015109005 | 7/2015 |
| WO | 2017130682 | 8/2017 |

OTHER PUBLICATIONS

"International Search Report and Written Opinion received in International Application No. PCT/2021/018188".

"International Search Report and Written Opinion received in International Application No. PCT/US2021/018155".

"International Search Report and Written Opinion received in International Application No. PCT/US2021/018187".

"International Search Report and Written Opinion received in International Application No. PCT/US2021/018190".

"scienceofpeople.com/emojis", https://www.scienceofpeople.com/emojis/ (accessed May 27, 2021).

Hebert, et al., "Spatiotemporal image correlation spectroscopy (STICS) theory, verification, and application to protein velocity mapping in living CHO cells", Biophysical journal 88, No. 5 (2005): 3601-3614.

Kheng, et al., "Image Processing", https://www.comp.nus.edu.sg/~cs4243/lecture/imageproc.pdf, Mar. 9, 2014.

Mita, et al., "High-Speed and Compact Quenching Circuit for Single-Photon Avalanche Diodes", IEEE Transactions on Instrumentation and Measurement, vol. 57, No. 3, Mar. 2008 pp. 543-547.

Puszka, et al., "Time-resolved diffuse optical tomography using fast-gated single-photon avalanche diodes", Biomedical optics express, 2013, vol. 4, No. 8, pp. 1351-1365 (Year: 2013).

Sneha, et al., "Understanding Correlation", https://www.allaboutcircuits.com/technical-articles/understanding-correlation/, Jan. 4, 2017.

Takai, et al., "Single-Photon Avalanche Diode with Enhanced NIR-Sensitivity for Automotive LIDAR Systems", Sensors, 2016, 16(4): 459, pp. 1-9 (Year: 2016).

Xu, et al., "A 655 µW Silicon Photomultiplier-Based NIRS/EEG/EIT Monitoring ASIC for Wearable Functional Brain Imaging", IEEE Transactions on Biomedical Circuitsand Systems, IEEE, US, vol. 12, No. 6, Dec. 1, 2018.

Zucconi, et al., "The Autocorrelation Function", https://www.alanzucconi.com/2016/06/06/autocorrelation-function/, Jun. 6, 2016.

SPC3 Single Photon Counting Camera, Micro Photon Devices S.r.l. SPC3 User Manual Version 1.1.0—Nov. 2015.

Andor Learning Centre, et al., Intensified CCD Cameras, http://www.andor.com/learning-academy/intensified-ccd-cameras-the-technology-behind-iccds as viewed Jun. 7, 2019.

Borycki, et al., Interferometric Near-Infrared Spectroscopy (iNIRS) for determination of optical and dynamical properties of turbid media, Opt. Express 24, 329 (2016).

Durduran, et al., Diffuse correlation spectroscopy for non-invasive, micro-vascular cerebral blood flow measurement, Neuroimage, 2014—Elsevier https://www.sciencedirect.com/science/article/pii/S105381191300654X.

Newport, et al., Balanced Optical Receivers, https://www.newport.com/c/balanced-photoreceivers as viewed Jun. 7, 2019.

Photon Force Ltd, et al., Time-Resolved Photon-Counting Camera, https://www.photon-force.com/pf32-time-resolved-single-photon-counting-camera/ as viewed Jun. 7, 2019.

Sutin, Jason et al., Time-domain diffuse correlation spectroscopy, vol. 3, No. 9 / Sep. 2016 / Optica 1006-1013.

Thor Labs, et al., Balanced Detectors, https://www.thoriabs.com/navigation.cfm?guide_id=2120 as viewed Jun. 7, 2019.

Zarychta, Katarzyna et al., Time-resolved diffusing wave spectroscopy with a CCD camera, Aug. 2, 2010 / vol. 18, No. 16 / Optics Express 16289.

Zhou, et al., Highly parallel, interferometric diffusing wave spectroscopy for monitoring cerebral blood flow dynamics, Optica, 2018 https://www.osapublishing.org/optica/abstract.cfm?uri=optica-5-5-518.

\* cited by examiner

NON-INVASIVE MEASUREMENT SYSTEMS WITH SINGLE-PHOTON COUNTING CAMERA

RELATED APPLICATIONS

The present application claims priority under 35 U.S.C. § 119(e) to U.S. Provisional Patent Application No. 62/699,656, filed Jul. 17, 2018, and to U.S. Provisional Patent Application No. 62/772,584, filed Nov. 28, 2018. These applications are incorporated herein by reference in their respective entireties.

BACKGROUND INFORMATION

Detection of brain activity is useful for medical diagnostics, imaging, neuroengineering, brain-computer interfacing, and a variety of other diagnostic and consumer-related applications. For example, cerebral blood flow ensures the delivery of oxygen and needed substrates to tissue, as well as removal of metabolic waste products. Thus, detection and quantification of cerebral blood flow is useful for diagnosis and management of any brain injury or disease associated with ischemia or inadequate vascular autoregulation.

As another example, there is an increasing interest in measuring event-related optical signals (also referred to as fast-optical signals). Such signals are caused by changes in optical scattering that occur when light propagating through active neural tissue (e.g., active brain tissue) is perturbed through a variety of mechanisms, including, but not limited to, cell swelling, cell volume change, cell displacement, changes in membrane potential, changes in membrane geometry, ion redistribution, birefringence changes, etc. Because event-related optical signals are associated with neuronal activity, rather than hemodynamic responses, they may be used to detect brain activity with relatively high temporal resolution.

Various optical-based measurement techniques, such as continuous wave diffusive correlation spectroscopy (DCS), time domain DCS, and interferometric near-infrared spectroscopy (iNIRS), have been used to detect brain activity by detecting speckle patterns created from mutual interference of scattered light. However, these measurement techniques disadvantageously utilize a single detector (e.g., a photodetector) or a conventional charge-coupled device (CCD) camera, which are not sensitive nor fast enough to provide a robust measure of the rate of rapid speckle pattern variations.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
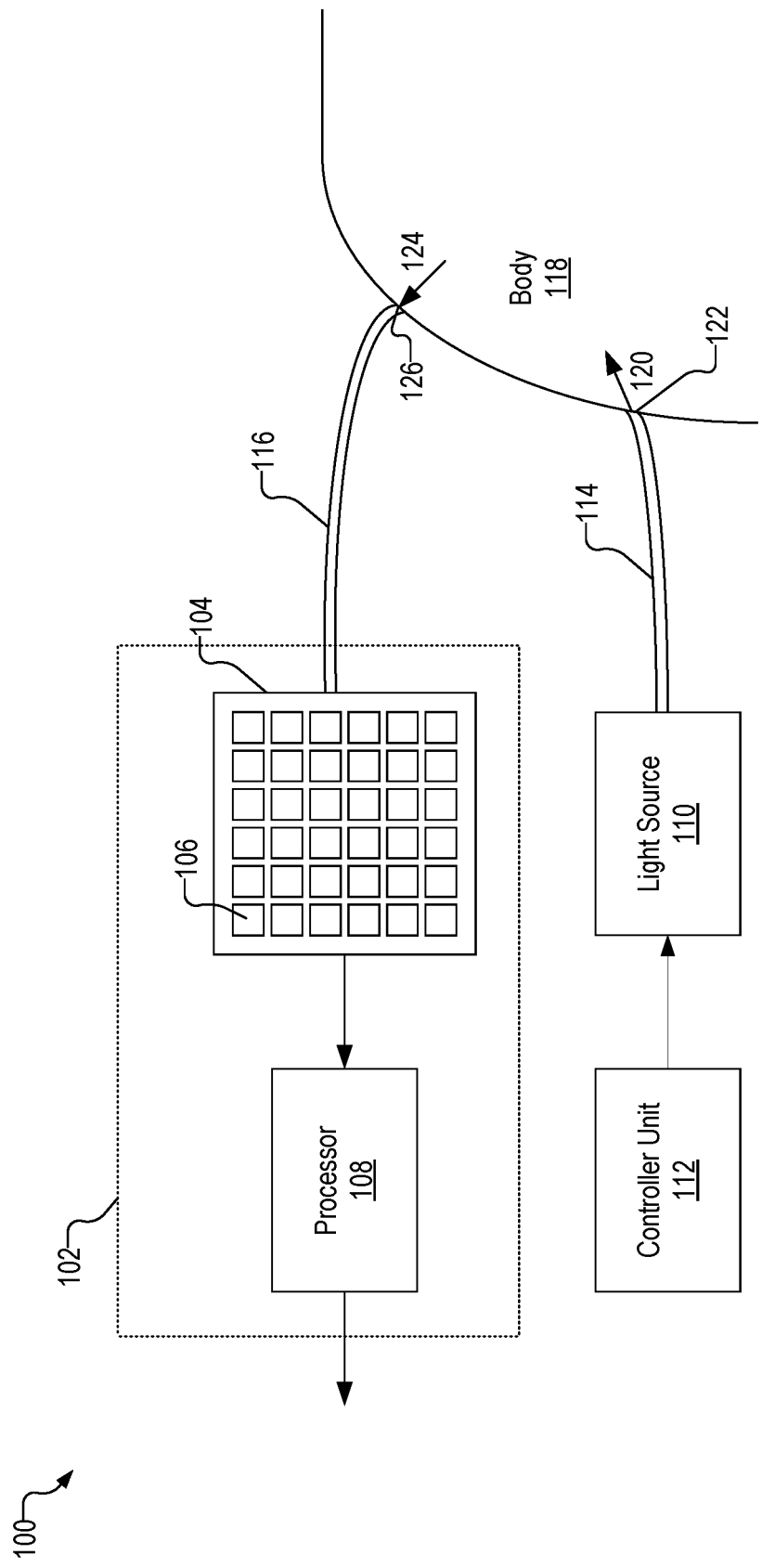
FIG. 1 shows an exemplary configuration in which an SPCC-based DCS measurement system is configured to measure a speckle pattern according to principles described herein.

Diffusive correlation spectroscopy (DCS) measurement systems and methods are described herein. The DCS measurement systems described herein may facilitate measurement of activity and event-related optical signals in a body (e.g., the brain) with improved sensitivity, accuracy, and resolution compared to conventional DCS measurement systems.

In some examples, as will be described in more detail below, a light source (e.g., a laser diode) generates coherent light that enters a body (e.g., a head of a subject) at an input location. The incident light may be continuous light, a sequence of light pulses, and/or a chirped beam, and scatters through many different optical paths within the body. Because of its high coherence, the light emerges from the body with the ability to interfere with itself to produce an interference pattern at one or more output locations. This interference pattern takes the form of a fully developed speckle pattern that rapidly varies at the one or more output locations. The DCS measurement systems described herein may measure the rapidly varying speckle pattern by determining correlation measurement values (e.g., temporal and/or spatial correlation measurement values) representative of speckle decorrelation (i.e., how speckles within the speckle pattern vary with respect to time and/or space).

The DCS measurement systems described herein utilize intensified charge-coupled device (ICCD) image sensors and/or single-photon counting cameras (SPCCs) to measure speckle patterns created from mutual interference of scattered light. As will be made apparent herein, ICCD-based and SPCC-based DCS measurement systems may advantageously be able to measure rapidly varying speckle patterns and thereby facilitate detection of brain activity, event-related optical signals, and other types of physiological activity, e.g., physiologically dependent optical parameters in the human body, animal body, and/or biological tissue.

In one example, an ICCD-based continuous wave DCS measurement system includes a microchannel plate, a CCD image sensor optically coupled to an output of the microchannel plate, and a processor coupled to an output of the CCD image sensor. The microchannel plate is configured to receive and amplify coherent continuous light that exits a body after the light enters and scatters within the body. The CCD image sensor includes a plurality of photodetectors and is configured to use the photodetectors to detect the amplified light during a sequence of gated time intervals and generate a plurality of electronic signals representative of the amplified light. The processor is configured to generate, based on the electronic signals, a sequence of speckle pattern image frames corresponding to the gated time intervals. The processor may be further configured to generate, based on the sequence of speckle pattern image frames, a correlation map representative of speckle decorrelation associated with the amplified light.

As another example, an SPCC-based continuous wave DCS measurement system includes an SPCC and a processor coupled to an output of the SPCC. The SPCC includes an array of single-photon avalanche diode (SPAD) detectors configured to detect, during a sequence of gated time intervals, coherent continuous light that exits a body after the light enters and scatters within the body. The SPAD detectors are further configured to output a plurality of electronic signals representative of the detected light. The processor is configured to generate, based on the electronic signals, a sequence of speckle pattern image frames corresponding to the gated time intervals. The processor may be further configured to generate, based on the sequence of speckle pattern image frames, a correlation map representative of speckle decorrelation associated with the light.

As another example, an ICCD-based time domain DCS measurement system includes a microchannel plate, a CCD image sensor optically coupled an output of to the microchannel plate, and a processor coupled to an output of the CCD image sensor. The microchannel plate, when presented with a sequence of pulses of coherent light that exit a body after the light enters and scatters within the body, is gated to receive and amplify the light during a first capture period starting at a first time delay within each of the pulses, the first capture period being shorter in duration than each pulse included in the sequence of pulses. The CCD image sensor includes a plurality of photodetectors and is configured to use the photodetectors to detect the amplified light received by the microchannel plate during the first capture period and generate a first set of electronic signals representative of the amplified light received by the microchannel plate during the first capture period. The processor is configured to generate, based on the first set of electronic signals, a first sequence of speckle pattern image frames corresponding to the first time delay. The processor may be further configured to generate, based on the first sequence of speckle pattern image frames, a correlation map representative of speckle decorrelation associated with the amplified light detected during the first capture period.

As another example, an SPCC-based time domain DCS measurement system includes an SPCC and a processor coupled to an output of the SPCC. The SPCC includes an array of SPAD detectors that, when presented with a sequence of pulses of coherent light that exit a body after the light enters and scatters within the body, are gated to detect the light during a first capture period starting at a first time delay within each of the pulses, the first capture period shorter in duration than each pulse included in the sequence of pulses and generate a first set of electronic signals representative of the light detected during the first capture period starting at the first time delay within each of the pulses. The processor is configured to generate, based on the first set of electronic signals, a first sequence of speckle pattern image frames corresponding to the first time delay. The processor may be further configured to generate, based on the first sequence of speckle pattern image frames, a correlation map representative of speckle decorrelation associated with the light detected during the first capture period.

As another example, an ICCD-based iNIRS detection system includes a microchannel plate, a CCD image sensor optically coupled an output of to the microchannel plate, and a processor coupled to an output of the CCD image sensor. The microchannel plate, when presented with an interference signal representative of a combination of a chirped sample beam after the chirped sample beam enters and exits a body and a chirped reference beam, is gated at a first frequency to periodically receive and amplify the interference signal during a plurality of capture periods. The CCD image sensor includes a plurality of photodetectors and is configured to use the photodetectors to detect, during a first camera exposure time period, the amplified interference signal received by the microchannel plate during the plurality of capture periods and generate a first set of electronic signals representative of the amplified interference signal received by the microchannel plate during the plurality of capture periods. The processor is configured to generate, based on the first set of electronic signals, a first speckle pattern image frame corresponding to the first frequency. The processor may be further configured to generate, based on the first speckle pattern image frame, a correlation map representative of speckle decorrelation associated with the amplified interference signal detected during the capture periods.

FIG. 1 shows an exemplary configuration 100 in which an SPCC-based DCS measurement system 102 is configured to measure a speckle pattern. As shown, SPCC-based DCS measurement system 102 includes an SPCC 104 that includes an array of SPAD detectors (e.g., SPAD detector 106) and a processor 108 coupled to an output of SPCC 104. Other components included in configuration 100 (e.g., a light source 110, a controller unit 112, and optical fibers 114 and 116) are not shown to be included in DCS measurement system 102 in FIG. 1. However, one or more of these components may, in certain embodiments, be considered to be a part of DCS measurement system 102.

SPCC 102 is a detector array that includes a plurality of pixels (e.g., around 1000 pixels). Each pixel is implemented by one or more of SPAD detectors 106, which may each be implemented by one or more SPAD circuits, an analogue front-end, and digital processing electronics. If there is more than one SPAD detector and circuit per pixel, then the detected signal from each of the SPAD detectors and circuits are combined in an analog fashion to produce one analog output per pixel. SPCC 102 may be implemented by an on-chip integrated device and provides single-photon sensitivity, high electronic noise immunity, and fast readout speed. In some examples, SPCC 102 may alternatively include a plurality of avalanche photodiodes in place of the SPAD circuits.

Light source 110 may be implemented by any suitable component configured to generate and emit high coherence light (e.g., light that has a coherence length of at least 5 centimeters) at a predetermined center wavelength. For example, light source 110 may be implemented by a high-coherence laser diode.

As will be illustrated below, in some examples, the light emitted by light source 110 includes coherent continuous light. In other examples, the light emitted by light source 110 includes a sequence of pulses of coherent light. In yet other examples, the light emitted by light source 110 includes a chirped sample beam.

Light source 110 is controlled by controller unit 112, which may be implemented by any suitable hardware (e.g., computing device, integrated circuit, etc.), firmware, software, or any combination thereof as may serve a particular implementation. Although all of the functionality of controller unit 112 is described herein as being performed by a single component, such functionality may be distributed amongst several components as may serve a particular implementation. In some examples, controller unit 112 is configured to control light source 110 by turning light source 110 on and off and/or setting an intensity of light generated by light source 110. Controller unit 112 may be manually operated by a user, or may be programmed to control light source 110 automatically.

Light emitted by light source 110 travels via an optical fiber 114 (e.g., a single-mode fiber or a multi-mode fiber) to a body 118 of a subject. In some implementations, body 118 is a head or any other body part of a human or other animal. Alternatively, body 118 may be a non-living object. For illustrative purposes, it will be assumed in the examples provided herein that body 118 is a human head.

As indicated by arrow 120, the light emitted by light source 110 enters body 118 at a first location 122 on body 118. To this end, a distal end of optical fiber 114 may be positioned at (e.g., right above or physically attached to) first location 122 (e.g., to a scalp of the subject). In some examples, the light may emerge from optical fiber 114 and spread out to a certain spot size on body 118 to fall under a predetermined safety limit.

After the light enters body 118, the light scatters through many different optical paths within body 118. The light emerges from body 118 at various locations. For example, as illustrated by arrow 124, the light may exit from body 118 at location 126, which is different than location 122. Because of its high coherence, the light may interfere with itself to produce an interference pattern in the form of a fully developed speckle pattern at location 126.

As shown, a proximal end of optical fiber 116 (e.g., a multi-mode optical fiber) is positioned at (e.g., right above or physically attached to) output location 126. In this manner, optical fiber 116 may collect light as it exits body 124 at location 126 and carry the light to photodetector array 104. The light may pass through one or more lenses and/or other optical elements (not shown) that direct the light onto each of the SPAD detectors 106 included in SPCC 104.

SPAD detectors 106 may detect the light and output a plurality of electronic signals representative of the detected light in a variety of different ways that will be described herein.

Processor 108 may be implemented by hardware (e.g., one or more physical processing (e.g., computing) devices), software, firmware, or any suitable combination thereof. In some examples, processor 108 may execute software configured to perform one or more of the operations described herein. Although all of the functionality of processor 108 is described herein as being performed by a single component, such functionality may be distributed amongst several components as may serve a particular implementation.

Processor 108 is configured to generate, based on the electronic signals output by SAD detectors 106, speckle pattern image frames. Processor 108 may be further configured to generate, based on the speckle pattern image frames, a correlation map representative of speckle decorrelation associated with the light. These operations performed by processor 108 will be described in more detail below.

Figure 2:
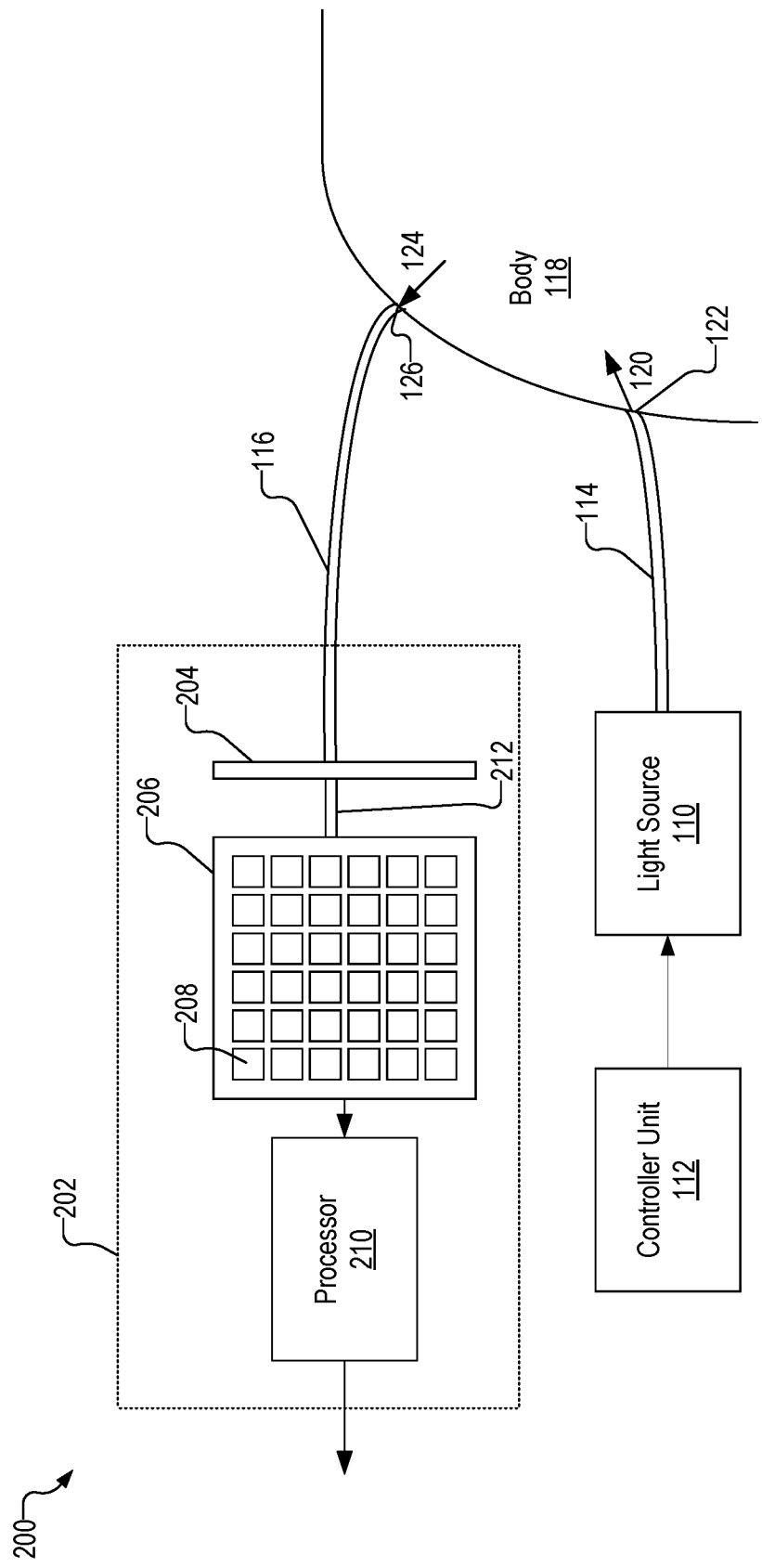
FIG. 2 shows an exemplary configuration in which an ICCD-based DCS measurement system is configured to measure a speckle pattern according to principles described herein.

FIG. 2 shows an exemplary configuration 200 in which an ICCD-based DCS measurement system 202 is configured to measure a speckle pattern. As shown, ICCD-based DCS measurement system 202 includes a microchannel plate 204, a CCD image sensor 206 that includes a plurality of photodetectors (e.g., photodetector 208), and a processor 210. Other components shown in configuration 200 are similar to those shown and described in connection with FIG. 1. For example, configuration 200 includes light source 110, controller unit 112, and optical fibers 114 and 116.

Microchannel plate 204 is configured to receive and amplify light that exits body 118. In this manner, microchannel plate 204 may enhance the light before the light is detected by CCD image sensor 204. Microchannel plate 204 may enhance the light through the process of electron multiplication. As will be described below, microchannel plate 204 may be time gated (e.g., voltage time gated), which enables ultrafast temporal signal measurement. This is particularly useful in measuring DCS signals, which are weak and highly dynamic.

Light amplified by microchannel plate 204 may be directed to CCD image sensor 206 by way of optical path 212, which may be implemented in any suitable manner. CCD image sensor 206 may use photodetectors 208 to detect the amplified light and generate a plurality of electronic signals representative of the light. Photodetectors 208 may each be implemented by any suitable CCD or complementary metal-oxide semiconductor (CMOS) device as may serve a particular implementation.

Processor 210 is similar to processor 108. For example, processor 210 may be implemented by hardware (e.g., one or more physical processing (e.g., computing) devices), software, firmware, or any suitable combination thereof. In some examples, processor 210 may execute software configured to perform one or more of the operations described herein. Although all of the functionality of processor 210 is described herein as being performed by a single component, such functionality may be distributed amongst several components as may serve a particular implementation.

Processor 210 is configured to generate, based on the electronic signals output by CCD image sensor 206, speckle pattern image frames. Processor 210 may be further configured to generate, based on the speckle pattern image frames, a correlation map representative of speckle decorrelation associated with the amplified light detected by photodetectors 208. These operations performed by processor 210 will be described in more detail below.

Figure 3:
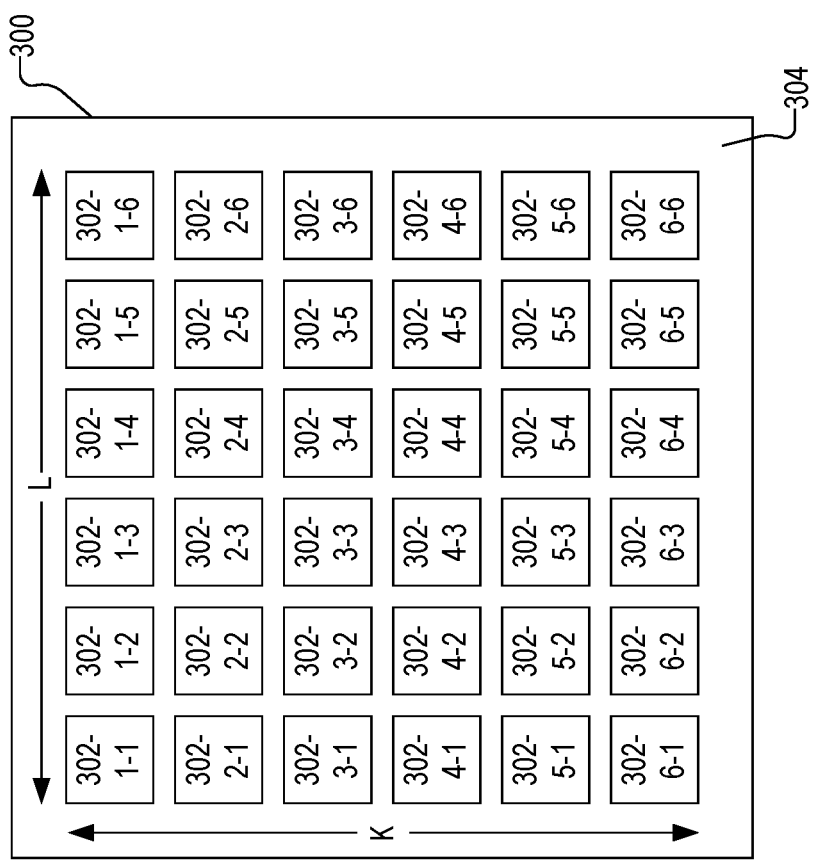
FIG. 3 illustrates an exemplary photodetector array according to principles described herein.

FIG. 3 illustrates an exemplary photodetector array 300 that includes a plurality of photodetectors 302. Photodetectors 302 may be representative of SPAD detectors 106 or of photodetectors 208. As shown, photodetectors 302 are arranged in a K by L array. In the example of FIG. 3, K and L are both equal to six. However, it will be recognized that photodetector array 300 may have any other suitable dimension where K times L is greater than one. In some examples, photodetector array 300 includes between 10 and 100,000 photodetectors.

Each photodetector 302 is labeled in FIG. 3 with indices that indicate a position (i.e., a row number and a column number) of the photodetector within photodetector array 300. For example, photodetector 302-1-1 is located in the first row and first column of photodetector array 300 and photodetector 302-6-6 is located in the sixth row and sixth column of photodetector array 300. As shown, each photodetector 302 may be disposed on a surface 304. Surface 304 may be implemented by a printed circuit board (PCB), an application-specific integrated circuit (ASIC), or any other suitable surface. In some examples, each photodetector 302 may be created via lithography on a silicon substrate, and then wire-bonded and packaged like other similar CMOS image chips.

Photodetectors 302 may each detect light that exits the body at location 126 and output an electronic signal representative of the detected light as a function of time. Because there are K times L photodetectors 302, photodetector array 300 outputs K times L electronic signals, where each photodetector 302 generates a different one of the K times L electronic signals.

To illustrate, a photodetector (e.g., photodetector 302-1-1) may detect light and output an electronic signal representative of the detected light as a function of time by detecting individual photons as they arrive at the photodetector and outputting an analog pulse each time a photon is detected. Hence, the electronic signal may include a series of pulses, where each pulse represents an arrival time of a photon. Alternatively, the photodetector may track how many photons arrive at the photodetector during a particular time interval (e.g., 10 microseconds) and output a count value representative of this number. In this case, the electronic signal output by the photodetector may include a series of values each representative of a number of photons that hit the photodetector during subsequent time intervals. Alternatively, the photodetector may detect amplified light output by a microchannel plate (e.g., microchannel plate 204).

Figure 4:
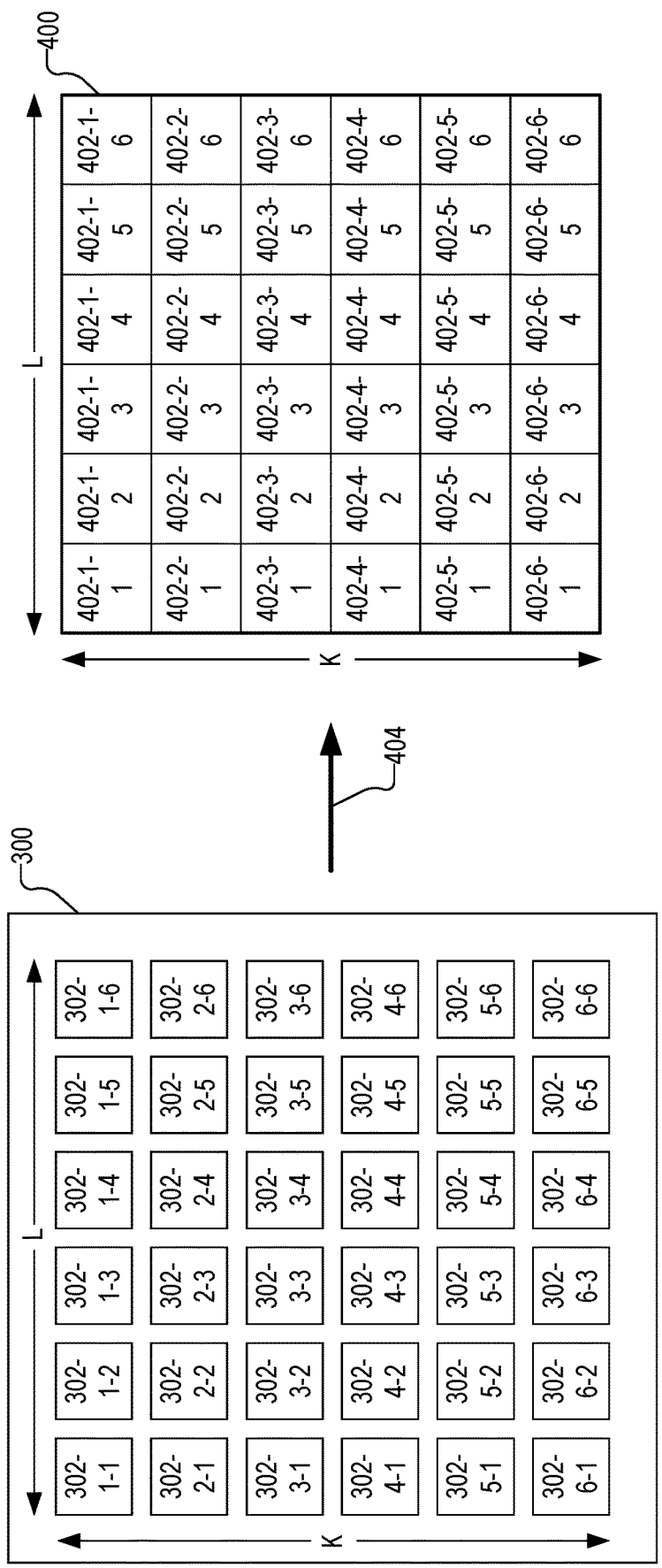
FIG. 4 shows a relationship between a photodetector array and a frame according to principles described herein.

As mentioned, a processor (e.g., processor 108 or processor 210) may generate, based on the electronic signals output by photodetectors 302, a sequence of speckle pattern image frames (or simply "frames"). For example, FIG. 4 shows a relationship between photodetector array 300 and a frame 400 generated by a processor sampling the electronic signals output by photodetector array 300 at a particular time. Each frame 400 accordingly represents a speckle pattern of light captured during a particular time interval.

As shown, frame 400 has K by L pixel locations 402. Each pixel location 402 is labeled in FIG. 4 with indices that indicate a position (i.e., a row number and a column number) of the pixel location 402 within frame 400. For example, pixel location 402-1-1 is located in the first row and first column of frame 400 and pixel location 402-6-6 is located in the sixth row and sixth column of frame 400. Each pixel location 402 corresponds to a location of a particular photodetector 302 in photodetector array 300. For example, pixel location 402-1-1 corresponds to a location of photodetector 302-1-1 in photodetector array 300, pixel location 402-1-2 corresponds to a location of photodetector 302-1-2 in photodetector array 300, etc.

As mentioned, frame 400 may be generated by processor 108 sampling the electronic signals output by photodetector array 300 at a particular time delay. This sampling is represented in FIG. 4 by arrow 404 and may be performed in accordance with any suitable signal processing heuristic. The sampling generates a plurality of digital sample values that are included in frame 400 at pixel locations 402. For example, frame 400 includes a digital sample value at pixel location 402-1-1 of an electronic signal output by photodetector 302-1-1, a digital sample value at pixel location 402-1-2 of an electronic signal output by photodetector 302-1-2, etc.

The processor (i.e., processor 108 or 210) may apply a plurality of temporal-based and/or spatial-based correlation measurement operations to the sample values in each of the frames generated by the processor. Based on the application of the temporal-based and/or spatial-based correlation measurement operations to the sample values, the processor may generate a plurality of correlation measure values for the light detected by photodetector array 300. The processor may include the plurality of correlation measure values in one or more correlation maps. Exemplary manners in which correlation measure values and correlation maps are generated are described in in U.S. Provisional Application No. 62/717,664, filed Aug. 10, 2018, the contents of which are hereby incorporated by reference in their entirety.

Various configurations in which SPCC-based DCS measurement system 102 and ICCD-based DCS measurement system 202 are configured to measure speckle patterns will now be described.

Figure 5:
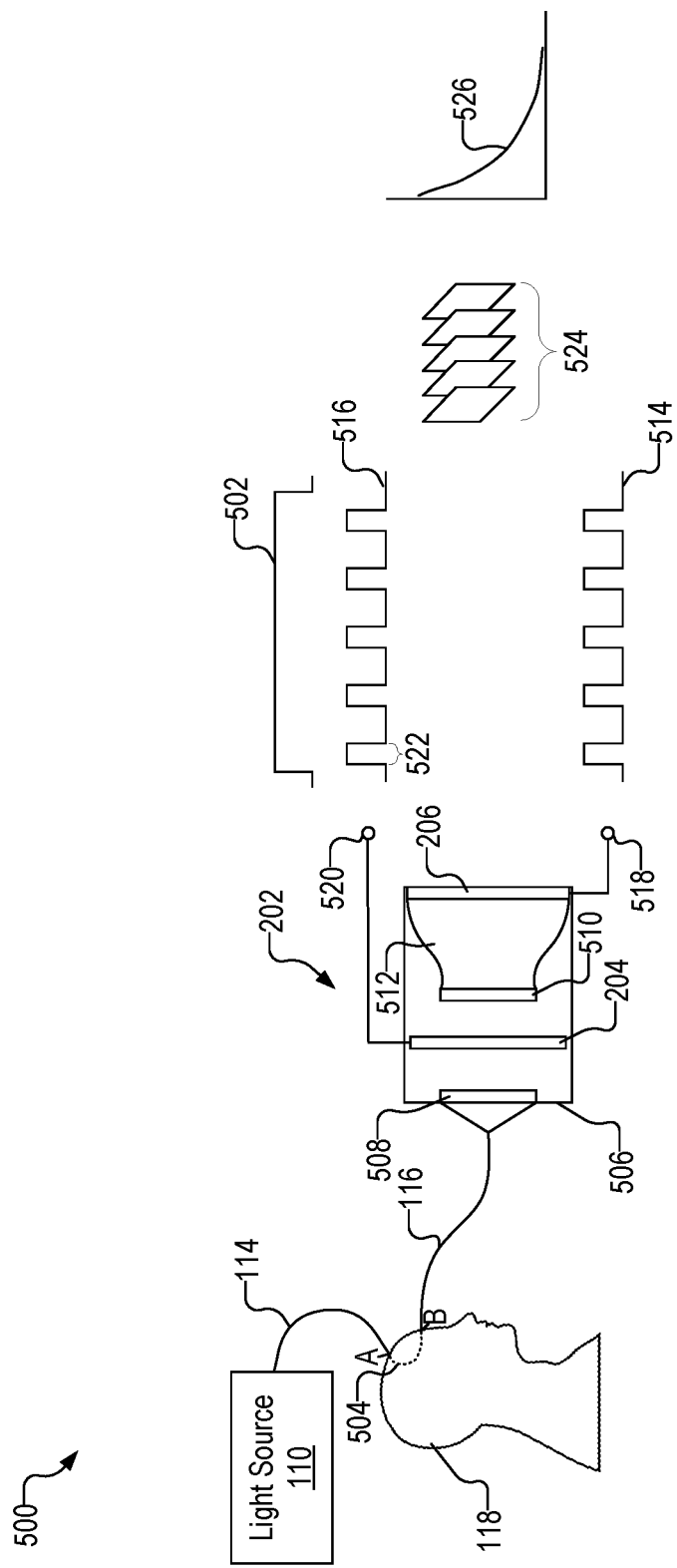
FIG. 5 illustrates an exemplary ICCD-based continuous wave DCS measurement configuration according to principles described herein.

FIG. 5 illustrates an exemplary ICCD-based continuous wave DCS measurement configuration 500 that utilizes ICCD-based DCS measurement system 202 to measure speckle patterns associated with light that exits a body 118 after the light enters and scatters within the body 118 (e.g., a user's head). In configuration 500, light source 110 generates and emits coherent continuous light 502 (e.g., a coherent continuous wave laser beam). Light 502 is illustrated in FIG. 5 as a single and relatively long pulse of continuous light (as opposed to other implementations described herein where the light comprises a sequence of relatively short pulses). Light 502 is conveyed to body 118 by way of an optical fiber 114. In the example of FIG. 5, body 118 is a human head.

As illustrated by dashed line 504, light 502 is shown entering at an enter location "A", scattering within body 118, and exiting body 118 at an exit location "B". Due to activity in body 118 (e.g., blood flow, event-related optical signals, etc.), highly dynamic (i.e., time-varying) speckle patterns are associated with the light that exits body 118.

The light 502 that exits body 118 at exit location "B" is conveyed to ICCD-based DCS measurement system 202 by way of optical fiber 116. As shown, ICCD-based DCS measurement system 202 is implemented by a CCD camera 506 that includes a photocathode 508, microchannel plate 204, phosphor 510, fiber optics 512, and CCD image sensor 206.

Photocathode 508 may be coated on an inside surface of an input window of CCD camera 506. When a photon generated by the exit light 502 conveyed by way of optical fiber 116 strikes photocathode 508, a photoelectron is emitted, which is drawn towards microchannel plate 204 by an electric field. Microchannel plate 204 may be implemented by a thin disc (e.g., 1 mm or less) comprising a plurality of glass channels each with a resistive coating. A high potential may be applied across microchannel plate 204, enabling the photoelectron to accelerate down one of the channels. When the photoelectron has sufficient energy, it dislodges secondary electrons from the channel walls. These electrons in turn undergo acceleration which results in a cloud of electrons exiting microchannel plate 204. This process may be referred to as electron multiplication, and results in microchannel plate 204 amplifying the light 502 that is incident upon CCD camera 506.

Amplified light 502 is conveyed from microchannel plate 204 to CCD image sensor 206 by way of phosphor 510 and fiber optics 512. CCD image sensor 206 is configured to use photodetectors 208 to detect amplified light 502 during a sequence of gated time intervals and to generate a plurality of electronic signals representative of the amplified light 502.

The gated time intervals may be generated in any suitable manner. For example, processor 210 or any other control unit may modulate an electronic camera trigger signal 514 that controls a camera exposure of CCD image sensor 506 and/or an electronic gating signal 516 that controls an operation of microchannel plate 204. Camera trigger signal 514 is provided at a camera trigger input 518 of CCD image sensor 206 and gating signal 516 is provided at gating input 520 of microchannel plate 204.

In the example of FIG. 5, both camera trigger signal 514 and gating signal 516 are modulated to be periodically on (e.g., by having a positive voltage) for a plurality of gated time intervals (e.g., gated time interval 522). When camera trigger signal 514 is on, CCD image sensor 206 is on and capturing amplified light 502. Alternatively, when camera trigger signal 514 is off (e.g., by having zero voltage), CCD image sensor 206 is off and not capturing amplified light 502. Likewise, when gating signal 516 is on (e.g., by having a positive voltage), microchannel plate 204 is on and detecting and amplifying light 502. Alternatively, when gating signal 516 is off (e.g., by having zero voltage), microchannel plate 204 is off and not detecting and amplifying light 502.

As shown, camera trigger signal 514 and gating signal 516 are synchronized to both be on at the same time. In some alternative embodiments, one of the signals (e.g., camera trigger signal 514) may be continuously on while the other signal (e.g., gating signal 514) modulates between being on and off.

The frequency at which the gated time intervals created by camera trigger signal 514 and/or gating signal 516 may be any suitable value as may serve a particular implementation. For example, camera trigger signal 514 and/or gating signal 516 may run at 1 kHz or higher.

Based on the electronic signals output by CCD image sensor 206, processor 210 generates a sequence of speckle pattern image frames 524 corresponding to the gated time intervals. Each frame 524 corresponds to one of the gated time intervals (e.g. the first frame shown in frames 524 may correspond to gated time interval 522) and may be similar in format to any of the frames described herein.

Processor 210 may compute a correlation between frames 524 to obtain an optical decorrelation curve 526 corresponding to body 118. For example, processor 210 may generate a correlation map based on frames 524 in any of the ways described herein.

Figure 6:
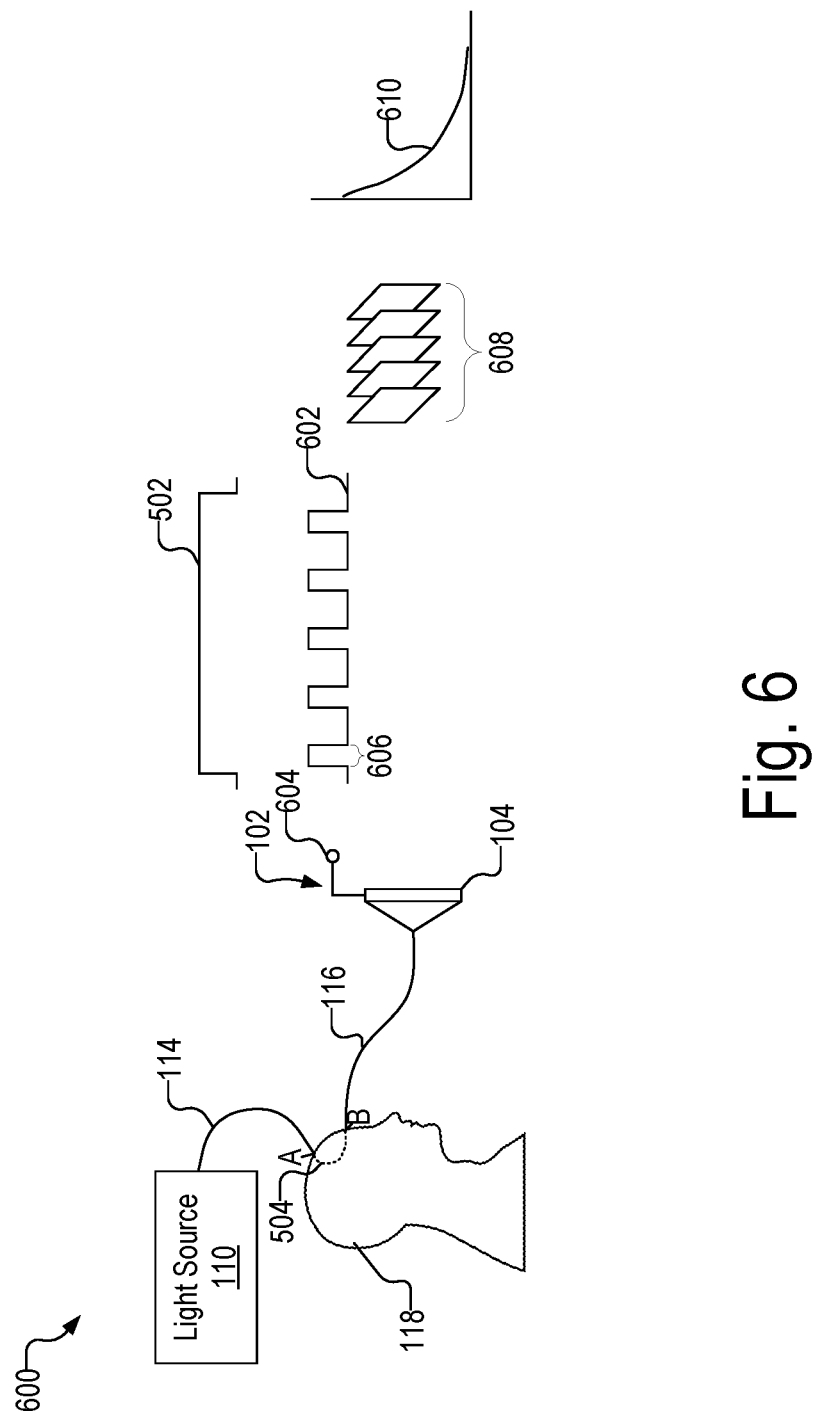
FIG. 6 illustrates an exemplary SPCC-based continuous wave DCS measurement configuration according to principles described herein.

FIG. 6 illustrates an exemplary SPCC-based continuous wave DCS measurement configuration 600 that utilizes SPCC-based DCS measurement system 102 to measure speckle patterns associated with light that exits a body 118 after the light enters and scatters within the body 118. As in configuration 500, light source 110 generates and emits coherent continuous light 502, which is conveyed to body 118 by way of optical fiber 114. As illustrated by dashed line 504, light 502 enters at enter location "A", scatters within body 118, and exits body 118 at exit location "B".

The light 502 that exits body 118 is conveyed to SPCC-based DCS measurement system 102 by way of optical fiber 116. As shown, SPCC-based DCS measurement system 102 is implemented by SPCC 104, which includes a plurality of SPAD detectors (not shown).

The SPAD detectors are configured to detect, during a sequence of gated time intervals, light 502 after light 502 scatters and exits body 118 at exit location "B". The SPAD detectors are further configured to output a plurality of electronic signals representative of detected light 502.

The gated time intervals may be generated in any suitable manner. For example, processor 108 or any other control unit may modulate a trigger signal 602 that controls an operation of SPCC 104. Trigger signal 602 is provided at a camera trigger input 604 of SPCC 104.

In the example of FIG. 6, trigger signal 602 is modulated to be periodically on (e.g., by having a positive voltage) for a plurality of gated time intervals (e.g., gated time interval 606). When trigger signal 602 is on, SPAD detectors included in SPCC 104 are on and capturing light 502. Alternatively, when trigger signal 602 is off (e.g., by having zero voltage), SPAD detectors included in SPCC 104 are off and not capturing light 502.

The frequency at which the gated time intervals created by trigger signal 602 may be any suitable frequency value as may serve a particular implementation. For example, trigger signal 602 may run at 1 kHz or higher.

Based on the electronic signals output by SPCC 104, processor 108 generates a sequence of speckle pattern image frames 608 corresponding to the gated time intervals. Each frame 608 corresponds to one of the gated time intervals (e.g. the first frame shown in frames 608 may correspond to gated time interval 606) and may be similar in format to any of the frames described herein.

Processor 108 may compute a correlation between frames 608 to obtain an optical decorrelation curve 610 corresponding to body 118. For example, processor 108 may generate a correlation map based on frames 608 in any of the ways described herein.

Figure 7:
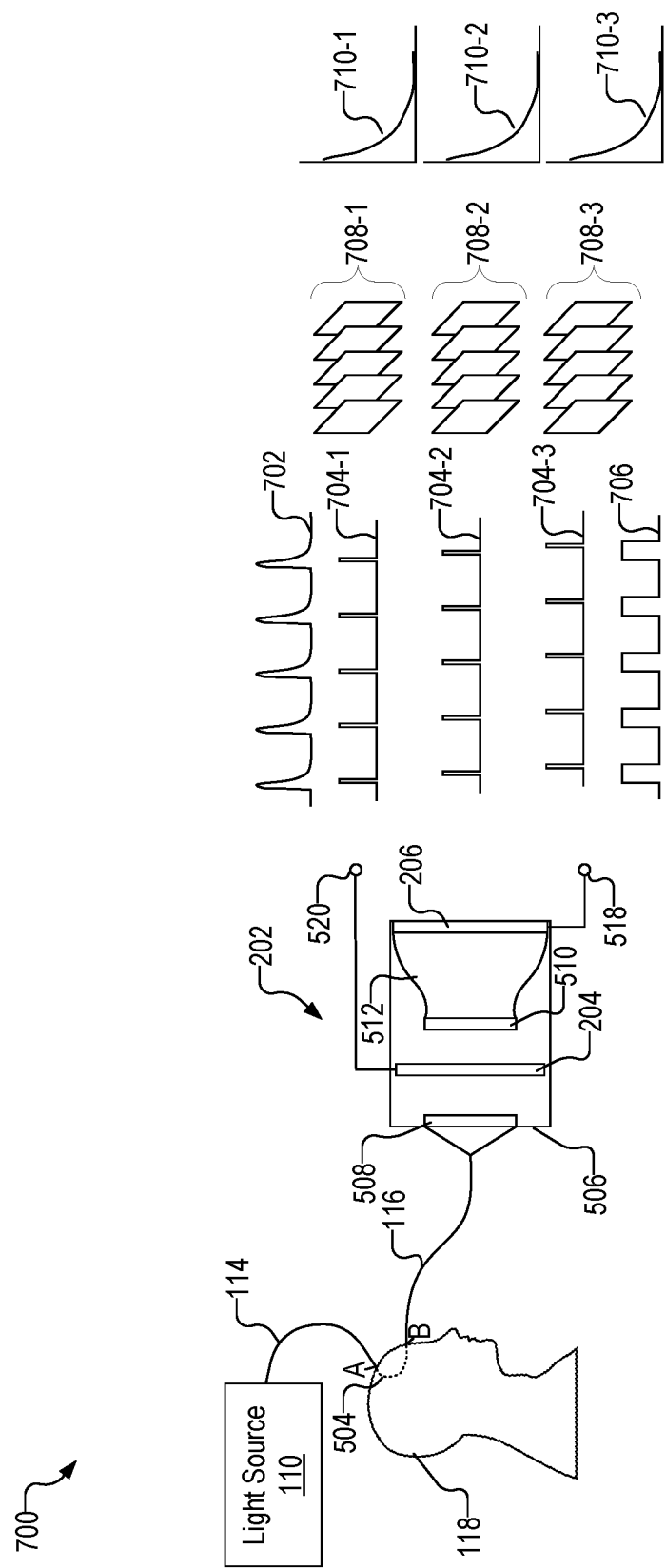
FIG. 7 illustrates an exemplary ICCD-based time domain DCS measurement configuration according to principles described herein.

FIG. 7 illustrates an exemplary ICCD-based time domain DCS measurement configuration 700 that utilizes ICCD-based DCS measurement system 202 to measure speckle patterns associated with light that exits a body 118 after the light enters and scatters within the body 118. In configuration 700, light source 110 generates and emits a sequence of pulses of coherent light. The pulses of light may have any suitable pulse width (e.g., 10 picoseconds (ps) or ranged from 1 ps to 1 nanosecond (ns)) and are conveyed to body 118 by way of optical fiber 114. The pulses are relatively short in duration and facilitate acquisition of time-of-flight information. Repetition rate of the pulses may be any suitable frequency value (e.g., 10 megahertz (MHz)).

As described in connection with FIG. 5, the light exits body 118 at an exit location after scattering within body 118. The light exits body 118 as pulses of coherent light 702 (also referred to as a light pulse train 702). Light pulse train 702 may be stretched compared to the input light pulses. For example, pulses in light pulse train 702 may have pulse widths of up to two ns. The camera frame rate can be 100 Hz or higher.

Light 702 is conveyed to ICCD-based DCS measurement system 202 by way of optical fiber 116. As shown, ICCD-based DCS measurement system 202 is implemented by CCD camera 506 that includes various components described in connection with FIG. 5.

Microchannel plate 204 is gated to receive and amplify light 702 during different sets of capture periods in each pulse of light 702. To this end, processor 108 (or any other control unit) may apply gating signals 704-1 through 704-3 at gating input 520 of microchannel plate 204 and a camera trigger signal 706 to camera trigger input 518 of CCD image sensor 206. Gating signals 704 may be applied concurrently or sequentially as may serve a particular implementation.

Figure 8:
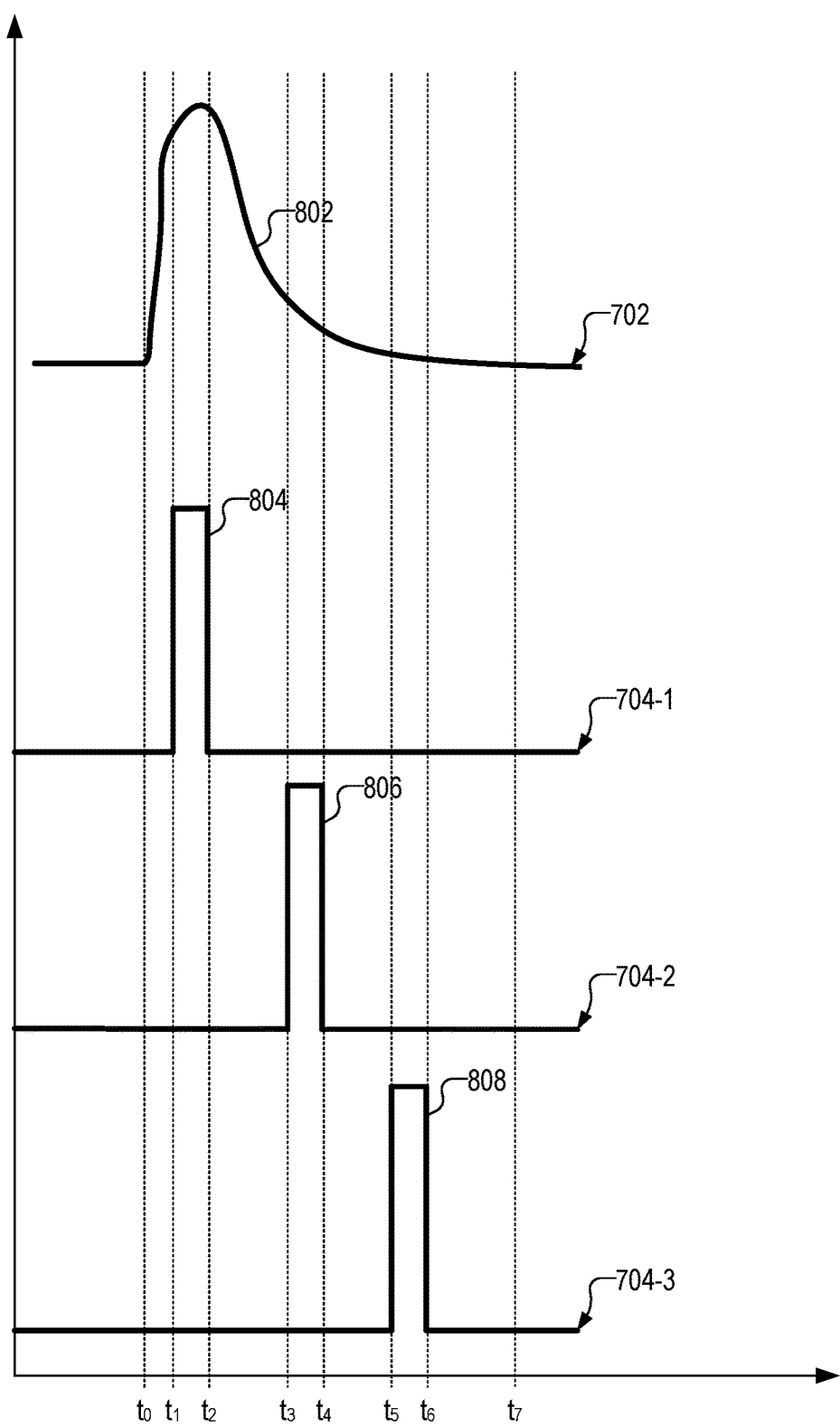
FIG. 8 shows a close up view of various pulses according to principles described herein.

Gating signals 704 and camera trigger signal 706 are configured to facilitate capture of light 702 during each the different capture periods. To illustrate, FIG. 8 shows a close up view of a first pulse 802 included in light pulse train 702, a first pulse 804 in gating signal 704-1, a first pulse 806 in gating signal 704-2, and a first pulse 808 in gating signal 704-3. Each of pulses 804-808 represent capture periods within which portions of light 702 in pulse 802 are detected and amplified by microchannel plate 204. As shown, the capture period represented by pulse 804 starts at a first time delay $t_1$ within pulse 802 (where the time delay is with respect to $t_0$, i.e., the beginning of pulse 802) and has a duration of $t_2-t_1$. The capture period represented by pulse 806 starts at a second time delay $t_3$ within pulse 802 and has a duration of $t_4-t_3$. The capture period represented by pulse 808 starts at a third time delay $t_5$ within pulse 802 and has a duration of $t_6-t_5$. Hence, each capture period represented by pulses 804-808 is shorter in duration than pulse 802 of light 702. The time delays and capture period durations may be set by processor 210 and/or any other computing device as may serve a particular implementation. For example, an exemplary pulse width of pulse 802 is about 3 ns and an exemplary time delay is around 100 ps.

Returning to FIG. 7, each pulse included in a particular gating signal 704 is associated with the same time delay. For example, each pulse included in gating signal 704-1 starts the same time delay after the beginning of one the pulses included in light 702. To this end, gating signals 704 may be synchronized with the light pulses emitted by light source 110.

The amplified light received and amplified during each of the capture periods represented in gating signals 704 is detected by CCD image sensor 206. CCD image sensor 206 outputs electronic signals representative of the amplified light. Processor 210 generates, based on the electronic signals, sequences of speckle pattern image frames 708 (e.g., frame sequence 708-1, frame sequence 708-2 and frame sequence 708-3). Each frame sequence 708 corresponds to a different time delay. To illustrate, frames included in frame sequence 708-1 represent speckle patterns detected at a first time delay within each pulse of light 702, frames included in frame sequence 708-2 represent speckle patterns detected at a second time delay within each pulse of light 702, and frames included in frame sequence 708-3 represent speckle patterns detected at a third time delay within each pulse of light 702.

Processor 210 may compute a correlation between frames 708-1 to obtain an optical decorrelation curve 710-1 (e.g., by computing a correlation map) associated with the first time delay, a correlation between frames 708-2 to obtain an optical decorrelation curve 710-2 (e.g., by computing a correlation map) associated with the second time delay, and a correlation between frames 708-3 to obtain an optical decorrelation curve 710-3 (e.g., by computing a correlation map) associated with the third time delay. By measuring the correlation between frames this manner, processor 210 may measure the decorrelation time of the optical field with a time-of-flight or path length associated with each of the different time delays.

Figure 9:
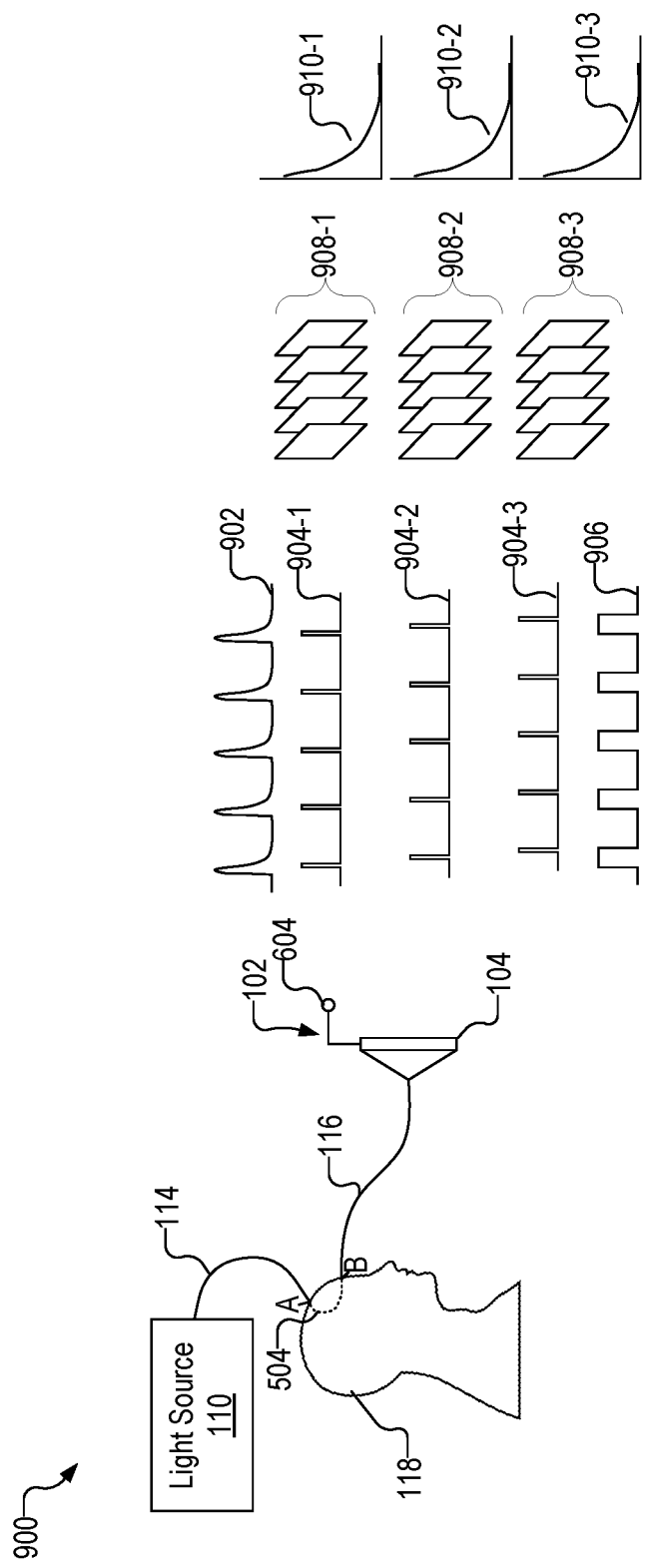
FIG. 9 illustrates an exemplary SPCC-based time domain DCS measurement configuration according to principles described herein.

FIG. 9 illustrates an exemplary SPCC-based time domain DCS measurement configuration 900 that utilizes SPCC-based DCS measurement system 102 to measure speckle patterns associated with light that exits a body 118 after the light enters and scatters within the body 118. As in configuration 700, light source 110 generates and emits a sequence of pulses of coherent light. The pulses of light are conveyed to body 118 by way of optical fiber 114. The pulses are relatively short in duration and facilitate acquisition of time-of-flight information.

As described in connection with FIG. 7, the light exits body 118 at an exit location "B" after scattering within body 118. The light exits body 118 as pulses of coherent light 902 (also referred to as a light pulse train 902). Light 902 is conveyed to SPCC-based DCS measurement system 102 by way of optical fiber 116. As shown, SPCC-based DCS measurement system 102 is implemented by SPCC 104, which includes a plurality of SPAD detectors (not shown).

SPAD detectors are gated to detect light 902 during different sets of capture periods in each pulse of light 902, as described in connection with FIG. 7. To this end, processor 108 (or any other control unit) may apply gating signals 904-1 through 904-3 at camera trigger input 604 of SPCC 104. A camera exposure signal 906 may also be applied to SPCC 104.

Gating signals 904 are similar to gating signals 704 and are each associated with a different time delay within each of the pulses of light 902. For example, each pulse included in gating signal 904-1 starts the same time delay after the beginning of one the pulses included in light 902. To this end, gating signals 904 may be synchronized with the light pulses emitted by light source 110.

The SPAD detectors in SPCC 104 output electronic signals representative of the light captured during each capture period. Processor 108 generates, based on the electronic signals, sequences of speckle pattern image frames 908 (e.g., frame sequence 908-1, frame sequence 908-2 and frame sequence 908-3). Each frame sequence 908 corresponds to a different time delay. To illustrate, frames included in frame sequence 908-1 represent speckle patterns detected at a first time delay within each pulse of light 902, frames included in frame sequence 908-2 represent speckle patterns detected at a second time delay within each pulse of light 902, and frames included in frame sequence 908-3 represent speckle patterns detected at a third time delay within each pulse of light 902.

Processor 108 may compute a correlation between frames 908-1 to obtain an optical decorrelation curve 910-1 (e.g., by computing a correlation map) associated with the first time delay, a correlation between frames 908-2 to obtain an optical decorrelation curve 910-2 (e.g., by computing a correlation map) associated with the second time delay, and a correlation between frames 908-3 to obtain an optical decorrelation curve 910-3 (e.g., by computing a correlation map) associated with the third time delay. By measuring the correlation between frames this manner, processor 108 may measure the decorrelation time of the optical field with a time-of-flight or path length associated with each of the different time delays.

Figure 10:
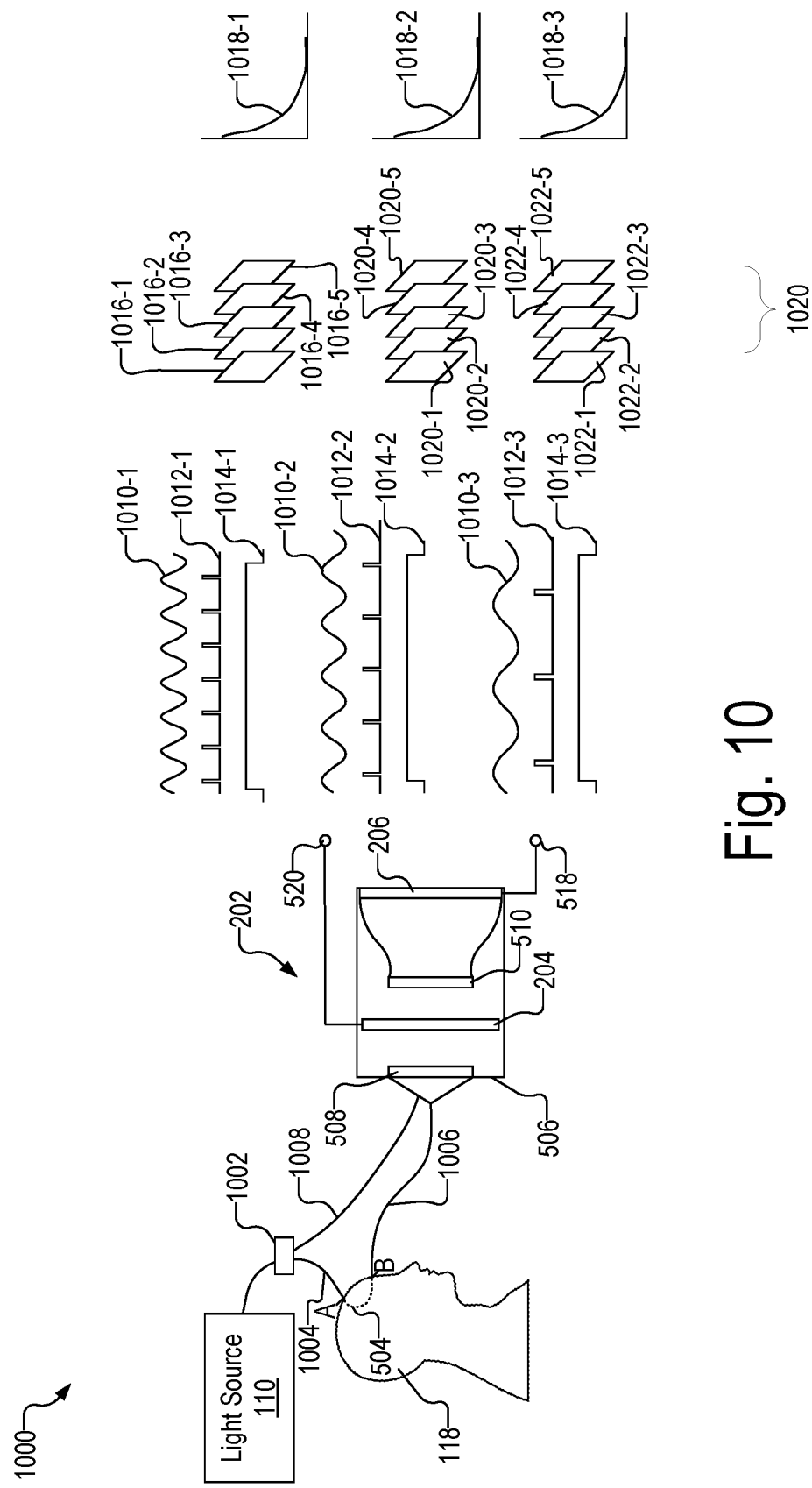
FIG. 10 illustrates an exemplary ICCD-based iNIRS detection configuration according to principles described herein.

FIG. 10 illustrates an exemplary ICCD-based iNIRS detection configuration 1000 that utilizes ICCD-based DCS measurement system 202. ICCD-based iNIRS detection configuration 1000 utilizes a frequency chirped light source to encode path-length information of DCS signals. With the interference with a chirp reference beam, the interference signals contain multiple frequencies, with each frequency associated with a path length of detected light. Therefore, by selectively measuring a frequency of interest, configuration 1000 is able to measure a DCS signal of a path length of interest. To this end, the time gating of microchannel plate 204 is modulated at a certain frequency, and the signals detected by CCD image sensor 206 are integrated over a time period shorter and comparable to the speckle decorrelation time. By repeating this process, configuration 1000 may obtain a stack of speckle pattern image frames at this frequency, which configuration 1000 uses to compute an optical decorrelation time at the corresponding path length or time-of-flight. To measure the decorrelation at a different path length, configuration 1000 may modulate microchannel plate 204 at a different frequency and repeat the above process.

In configuration 1000, light source 110 generates and emits a chirped light beam. The chirped light beam may have any suitable characteristic (e.g., a wavelength of 800 nm and a frequency chirp range of any value between 1 gigahertz (GHz) to 1 terahertz (THz)). The chirped light beam is input into an optical splitter 1002, which splits the chirped light beam into a chirped reference beam and a chirped sample beam. The chirped sample beam is conveyed to body 118 by way of an optical fiber 1004. As illustrated by dashed line 504, the chirped sample beam enters at an enter location "A", scatters within body 118, and exits body 118 at an exit location "B". The chirped sample beam that exits body 118 is conveyed to ICCD-based DCS measurement system 202 by way of an optical fiber 1006. The chirped reference beam output by optical splitter 1002 is conveyed directly to ICCD-based DCS measurement system 202 by way of an optical fiber 1008.

Due to the scattering within body 118, the chirped sample beam conveyed to ICCD-based DCS measurement system 202 has a different frequency than the chirped reference beam. Hence, the chirped sample beam and the chirped reference beam combine to create an interference signal. The interference signal may have an interference signal frequency of any value between 1 Hz and 1 GHz. Microchannel plate 204 is gated at different frequencies to periodically receive and amplify the interference signal during a plurality of capture periods.

For example, as shown, to detect and amplify a first frequency component of the interference signal (represented in FIG. 10 by signal 1010-1), processor 210 (or any other control unit) may gate microchannel plate 204 at the first frequency by applying a gating signal 1012-1 to gating input 520 of microchannel plate 204. Gating signal 1012-1 includes a plurality of pulses that occur at the first frequency. The duration of each pulse defines the capture periods during which microchannel plate 204 is on (i.e., during each pulse, microchannel plate 204 receives and amplifies interference signal 1010-1).

While gating signal 1012-1 is applied to gating input 520, a camera trigger signal 1014-1 is applied to camera trigger input 518 of CCD image sensor 206. As shown, camera trigger signal 1014-1 includes a relatively wide pulse (e.g., 100 microseconds), which causes CCD image sensor 206 to detect, during a first camera exposure time period defined by the relatively wide pulse (e.g., between 1 microsecond and 10 ms), amplified interference signal 1010-1 received by microchannel plate 204 during a plurality of capture periods defined by gating signal 1012-1. CCD image sensor 206 outputs a first set of electronic signals representative of the amplified interference signal 1010-1 received by microchannel plate 204 during the plurality of capture periods. Based on this first set of electronic signals, processor 210 generates a first speckle pattern image frame 1016-1 corresponding to the first frequency. This process may be repeated to generate additional speckle pattern image frames (e.g., frames 1016-2 through 1016-5). Processor 208 may then compute a correlation between frames 1016 to obtain an optical decorrelation curve 1018-1 (e.g., by computing a correlation map).

To detect and amplify a second frequency component of the interference signal (represented in FIG. 10 by signal 1010-2), processor 210 (or any other control unit) may gate microchannel plate 204 at the second frequency by applying a gating signal 1012-2 to gating input 520 of microchannel plate 204. Gating signal 1012-2 includes a plurality of pulses that occur at the second frequency. The duration of each pulse defines the capture periods during which microchannel plate 204 is on (i.e., during each pulse, microchannel plate 204 receives and amplifies interference signal 1010-2).

While gating signal 1012-2 is applied to gating input 520, a camera trigger signal 1014-2 is applied to camera trigger input 518 of CCD image sensor 206. Camera trigger signal 1014-2 causes CCD image sensor 206 to detect, during a second camera exposure time, amplified interference signal 1010-2 received by microchannel plate 204 during a plurality of capture periods defined by gating signal 1012-2. CCD image sensor 206 outputs a second set of electronic signals representative of the amplified interference signal 1010-2 received by microchannel plate 204 during the plurality of capture periods. Based on this second set of electronic signals, processor 210 generates a first speckle pattern image frame 1020-1 corresponding to the second frequency. This process may be repeated to generate additional speckle pattern image frames (e.g., frames 1020-2 through 1020-5). Processor 208 may then compute a correlation between frames 1020 to obtain an optical decorrelation curve 1018-2 (e.g., by computing a correlation map).

To detect and amplify a third frequency component of the interference signal (represented in FIG. 10 by signal 1010-3), processor 210 (or any other control unit) may gate microchannel plate 204 at the third frequency by applying a gating signal 1012-3 to gating input 520 of microchannel plate 204. Gating signal 1012-3 includes a plurality of pulses that occur at the third frequency. The duration of each pulse defines the capture periods during which microchannel plate 204 is on (i.e., during each pulse, microchannel plate 204 receives and amplifies interference signal 1010-3).

While gating signal 1012-3 is applied to gating input 520, a camera trigger signal 1014-3 is applied to camera trigger input 518 of CCD image sensor 206. Camera trigger signal 1014-3 causes CCD image sensor 206 to detect, during a third camera exposure time, amplified interference signal 1010-3 received by microchannel plate 204 during a plurality of capture periods defined by gating signal 1012-3. CCD image sensor 206 outputs a third set of electronic signals representative of the amplified interference signal 1010-3 received by microchannel plate 204 during the plurality of capture periods. Based on this third set of electronic signals, processor 210 generates a first speckle pattern image frame 1022-1 corresponding to the third frequency. This process may be repeated to generate additional speckle pattern image frames (e.g., frames 1022-2 through 1022-5). Processor 208 may then compute a correlation between frames 1022 to obtain an optical decorrelation curve 1018-3 (e.g., by computing a correlation map).

In some examples, any of the configurations described herein that are ICCD-based may be implemented using a balanced detector array. For example, a balanced detector array may be used to implement photodetectors included in CCD image sensor 206.

Figure 11:
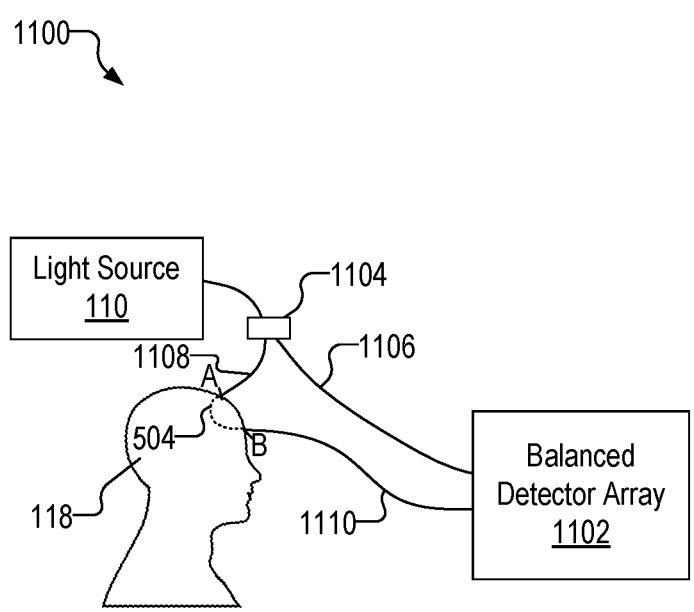
FIG. 11 illustrates an exemplary configuration in which a balanced detector array is configured to detect light according to principles described herein.

FIG. 11 illustrates an exemplary configuration 1100 in which a balanced detector array 1102 is configured to detect light. In configuration 1100, light source 110 (e.g., a single-mode laser) generates and emits a light that has a long coherence length (e.g., great than 1 meter). The light is input into a single-mode fiber coupler 1104, which splits the light into a sample beam and a reference beam. Fiber coupler 1104 may, for example, be a 1/99 fiber coupler such that the sample beam contains 99 percent of the energy in the light and the reference beam contains 1 percent of the energy in the light.

The reference beam is conveyed to a first input port of balanced detector array 1102 by way of an optical fiber 1106. The sample beam is conveyed to body 118 by way of an optical fiber 1108. As illustrated by dashed line 504, the sample beam enters and scatters within body 118 and exits body 118 at an exit location. The sample beam that exits body 118 is conveyed to a second input port of balanced detector array 1102 by way of an optical fiber 1110, which may be implemented by a multimode fiber with a relatively large core (e.g., a diameter of several hundred microns).

Figure 12:
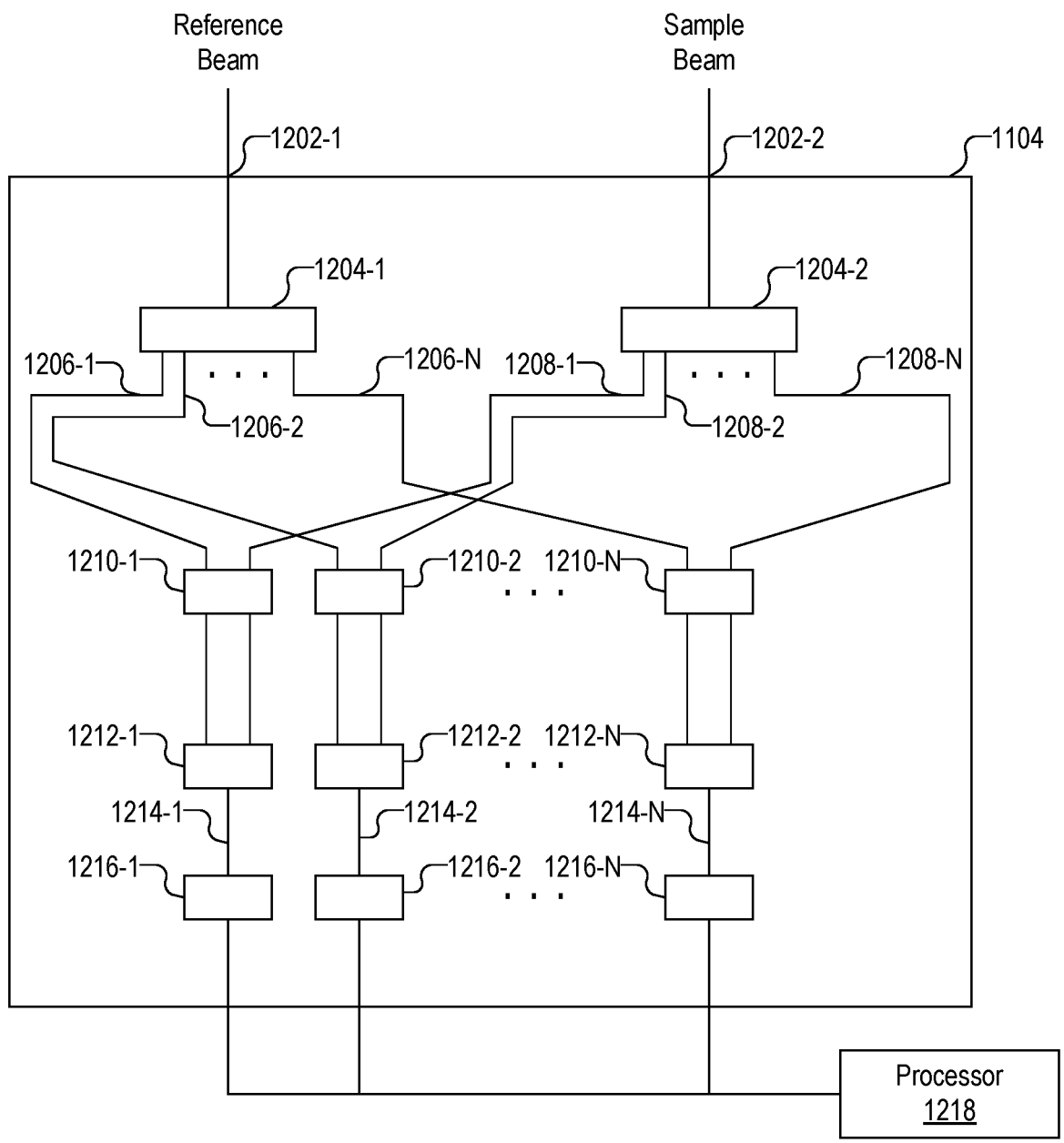
FIG. 12 depicts an inner structure of balanced detector array according to principles described herein.

FIG. 12 depicts an inner structure of balanced detector array 1104. As shown, the reference beam is input at a first input port 1202-1 and the sample beam is input at a second input port 1202-2. A 1×N fiber splitter 1204-1 splits the reference beam into N reference beams 1206 (e.g., reference beam 1206-1 through 1206-N). Likewise, 1×N fiber splitter 1204-2 splits the reference beam into N sample beams 1208 (e.g., sample beam 1206-1 through 1206-N). N may be any suitable number greater than one (e.g., several thousand).

As shown, reference beam 1206-1 and sample beam 1208-1 are input into a 2×2 fiber coupler 1210-1. Fiber coupler 1210-1 allows reference beam 1206-1 and sample beam 1208-1 to combine and interfere with one another. Other corresponding pairs of reference beams 1206 and sample beams 1208 are likewise input into other 2×2 fiber couplers (e.g., fiber coupler 1210-2 through 1210-N).

As shown, the outputs of fiber couplers are input into single balanced detectors 1212 (e.g., balanced detectors 1212-1 through 1212-N). Balanced detectors 1212 remove a common term between corresponding pairs of reference beams 1206 and sample beams 1208 and generate N output signals 1214. Output signals 1214 are digitized through analog-to-digital (ADC) convertors 1216 (e.g., ADC convertor 1216-1 through 1216-N) and provided to a processor 1218. Processor 1218 may be similar to any of the processors described herein and may be configured to generate spectral pattern image frames based on the digitized output signals 1214.

Any of the DCS measurement systems described herein may be implemented by or included in any suitable device. For example, any of the DCS measurement systems described herein may be included or housed in a non-invasive wearable device that a user may wear to perform one or more diagnostic, imaging, and/or consumer-related operations.

Figure 13:
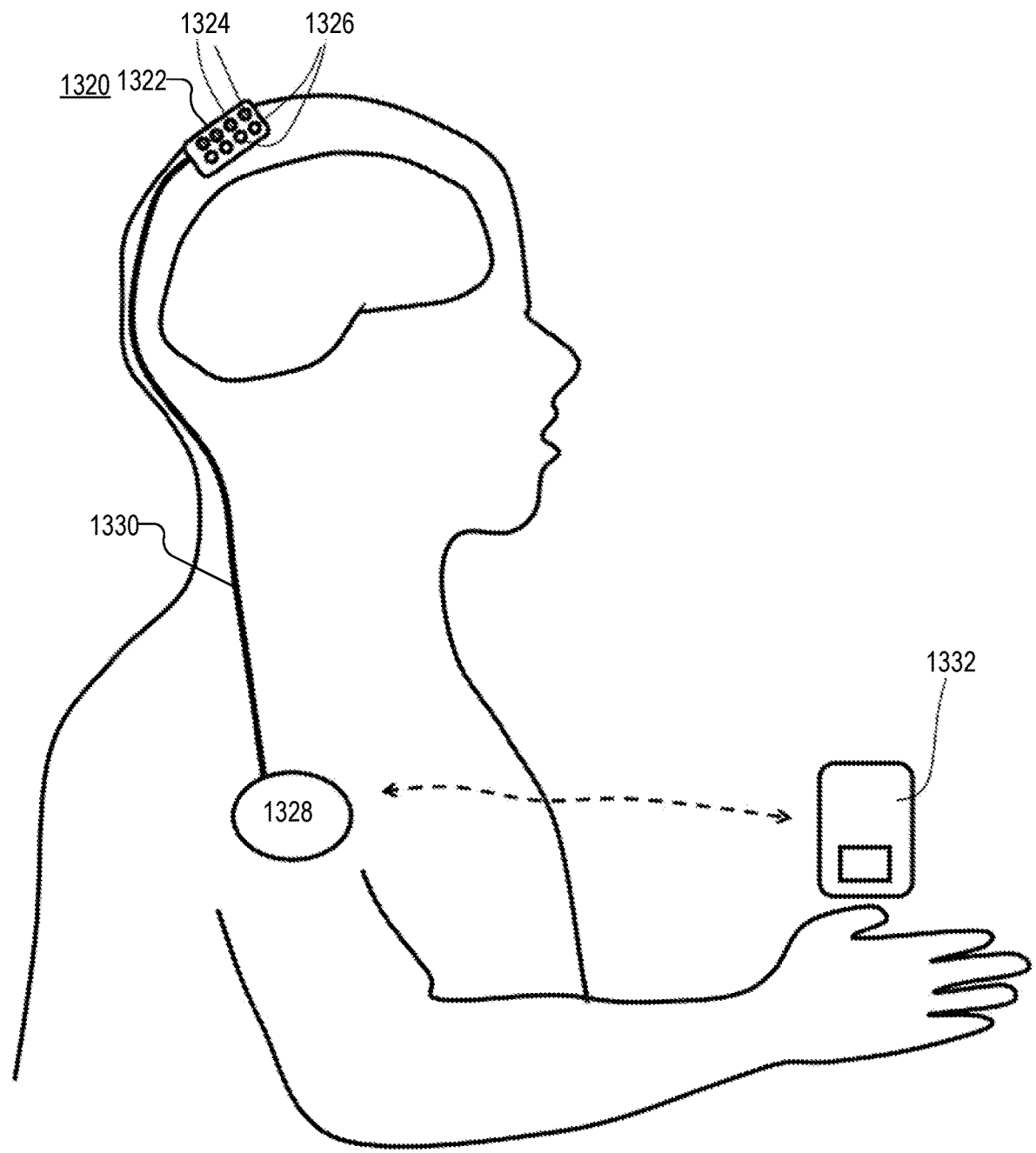
FIG. 13 shows an exemplary non-invasive wearable brain interface system according to principles described herein.

To illustrate, FIG. 13 shows an exemplary non-invasive wearable brain interface system 1320 ("brain interface system 1320") that may implement or house any of the components described herein. As shown, brain interface system 1320 includes a head-mountable component 1322 configured to be attached to a user's head. The head-mountable component 1322 may be shaped e.g., headband, helmet, hood, cap, beanie, or other shape adjustable to the body 118, e.g., user's head. Head-mountable component 1322 includes a plurality of DCS measurement systems 1324 (e.g., SPCC-based DCS measurement system 102 and/or ICCD-based DCS measurement system 202) and a plurality of light sources 1326 configured to generate light pulses. It will be recognized that in some alternative embodiments, head-mountable component 1322 may include a single DCS measurement system 1324 and/or a single light source 1326.

Brain interface system 1320 may further include a processor 1328 configured to communicate with (e.g., control and/or receive signals from) DCS measurement systems 1324 and light sources 1326 by way of a communication link 1330. Communication link 1330 may include any suitable wired and/or wireless communication link. Processor 1328 may include any suitable housing and may be located on the user's scalp, neck, shoulders, chest, or arm, as may be desirable. In some variations, processor 1328 may be integrated in the same assembly housing as DCS measurement systems 1324 and light sources 1326.

As shown, brain interface system 1320 may optionally include a remote processor 1332 in communication with processor 1328. For example, remote processor 1332 may store measured data from DCS measurement systems 1324 and/or processor 1328 from previous detection sessions. Power for photodetectors 1324, light sources 1326, and/or processor 1328 may be provided via a wearable battery (not shown). In some examples, processor 1328 and the battery may be enclosed in a single housing, and wires carrying power signals from processor 1328 and the battery may extend to DCS measurement systems 1324 and light sources 1326. Alternatively, power may be provided wirelessly (e.g., by induction).

The DCS measurement systems described herein may alternatively be included in a non-wearable device (e.g., a medical device and/or consumer device that is placed near the head or other body part of a user to perform one or more diagnostic, imaging, and/or consumer-related operations). The DCS measurement systems described herein may alternatively be included in a sub-assembly enclosure of a wearable invasive device (e.g., an implantable medical device for brain recording and imaging).

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 14:
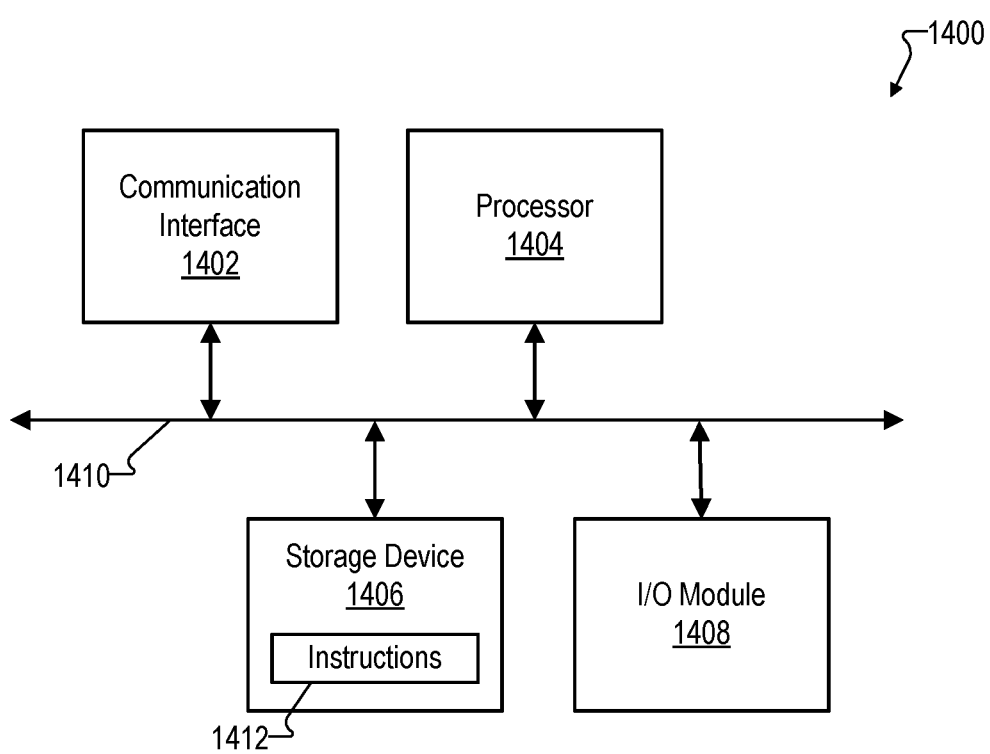
FIG. 14 illustrates an exemplary computing device according to principles described herein.

FIG. 14 illustrates an exemplary computing device 1400 that may be specifically configured to perform one or more of the processes described herein. As shown in FIG. 14, computing device 1400 may include a communication interface 1402, a processor 1404, a storage device 1406, and an input/output ("I/O") module 1408 communicatively connected one to another via a communication infrastructure 1410. While an exemplary computing device 1400 is shown in FIG. 14, the components illustrated in FIG. 14 are not intended to be limiting. Additional or alternative components may be used in other embodiments. Components of computing device 1400 shown in FIG. 14 will now be described in additional detail.

Communication interface 1402 may be configured to communicate with one or more computing devices. Examples of communication interface 1402 include, without limitation, a wired network interface (such as a network interface card), a wireless network interface (such as a wireless network interface card), a modem, an audio/video connection, and any other suitable interface.

Processor 1404 generally represents any type or form of processing unit capable of processing data and/or interpreting, executing, and/or directing execution of one or more of the instructions, processes, and/or operations described herein. Processor 1404 may perform operations by executing computer-executable instructions 1412 (e.g., an application, software, code, and/or other executable data instance) stored in storage device 1406.

Storage device 1406 may include one or more data storage media, devices, or configurations and may employ any type, form, and combination of data storage media and/or device. For example, storage device 1406 may include, but is not limited to, any combination of the non-volatile media and/or volatile media described herein. Electronic data, including data described herein, may be temporarily and/or permanently stored in storage device 1406. For example, data representative of computer-executable instructions 1412 configured to direct processor 1404 to perform any of the operations described herein may be stored within storage device 1406. In some examples, data may be arranged in one or more databases residing within storage device 1406.

I/O module 1408 may include one or more I/O modules configured to receive user input and provide user output. I/O module 1408 may include any hardware, firmware, software, or combination thereof supportive of input and output capabilities. For example, I/O module 1408 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1408 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1408 is configured to provide graphical data to a display for presentation to a user. The graphical data may be representative of one or more graphical user interfaces and/or any other graphical content as may serve a particular implementation.

In some examples, any of the systems, computing devices, processors, controller units, and/or other components described herein may be implemented by computing device 1400. For example, processor 108, processor 210, and controller unit 112 may be implemented by processor 1404.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A non-invasive measurement system comprising:
   a single-photon counting camera including an array of single-photon avalanche diode (SPAD) detectors configured to detect, during a sequence of gated time intervals, coherent continuous light that exits a body after the light enters and scatters within the body, and output a plurality of electronic signals representative of the detected light; and a processor coupled to an output of the single-photon counting camera and configured to generate, based on the electronic signals, a sequence of speckle pattern image frames corresponding to the gated time intervals.

2. The non-invasive measurement system of claim 1, wherein the processor is further configured to generate, based on the sequence of speckle pattern image frames, a correlation map representative of speckle decorrelation associated with the light.

3. The non-invasive measurement system of claim 2, wherein:
   each of the speckle pattern image frames includes K times L digital sample values at K by L pixel locations that correspond to locations of the SPAD detectors; and
   the processor is configured to generate the correlation map by
      applying a plurality of correlation measurement operations to the sample values in each of the speckle pattern image frames,
      generating, based on the application of the measurement operations to the sample values in each of the speckle pattern image frames, a plurality of measurement values for the light detected by the SPAD detectors, and
      including the plurality of measurement values in the correlation map.

4. The non-invasive measurement system of claim 1, further comprising a light source configured to generate the light.

5. The non-invasive measurement system of claim 4, further comprising an optical fiber coupled to an output of the light source and configured to convey the light to the body.

6. The non-invasive measurement system of claim 1, wherein the light is a laser signal.

7. The non-invasive measurement system of claim 1, further comprising an optical fiber coupled to the body and to the single-photon counting camera and configured to convey the light from the body to the SPAD detectors.

8. The non-invasive measurement system of claim 1, wherein the processor is configured to generate the sequence of gated time intervals by modulating a trigger signal that controls the single-photon counting camera.

9. The non-invasive measurement system of claim 1, further comprising a non-invasive wearable device for use by a user, wherein the single-photon counting camera and the processor are housed within the wearable device.

10. A non-invasive measurement system comprising:
    a single-photon counting camera including an array of single-photon avalanche diode (SPAD) detectors that, when presented with a sequence of pulses of coherent light that exit a body after the light enters and scatters within the body, are gated to detect the light during a first capture period starting at a first time delay within each of the pulses, the first capture period shorter in duration than each pulse included in the sequence of pulses, and generate a first set of electronic signals representative of the light detected during the first capture period starting at the first time delay within each of the pulses; and a processor coupled to an output of the single-photon counting camera and configured to generate, based on the first set of electronic signals, a first sequence of speckle pattern image frames corresponding to the first time delay.

11. The non-invasive measurement system of claim 10, wherein the processor is further configured to generate, based on the first sequence of speckle pattern image frames, a correlation map representative of speckle decorrelation associated with the light detected during the first capture period.

12. The non-invasive measurement system of claim 11, wherein:
    each of the speckle pattern image frames includes K times L digital sample values at K by L pixel locations that correspond to locations of the SPAD detectors; and
    the processor is configured to generate the correlation map by
        applying a plurality of correlation measurement operations to the sample values in each of the speckle pattern image frames,
        generating, based on the application of the measurement operations to the sample values in each of the speckle pattern image frames, a plurality of measurement values for the light detected by the SPAD detectors, and
        including the plurality of measurement values in the correlation map.

13. The non-invasive measurement system of claim 10, further comprising a light source configured to generate the light.

14. The non-invasive measurement system of claim 13, further comprising an optical fiber coupled to an output of the light source and configured to convey the light to the body.

15. The non-invasive measurement system of claim 10, wherein the light is a laser signal.

16. The non-invasive measurement system of claim 10, further comprising an optical fiber coupled to the body and to the single-photon counting camera and configured to convey the light from the body to the SPAD detectors.

17. The non-invasive measurement system of claim 10, wherein the processor is configured to generate the sequence of gated time intervals by modulating a gating signal that controls the single-photon counting camera.

18. The non-invasive measurement system of claim 10, further comprising a non-invasive wearable device for use by a user, wherein the single-photon counting camera and the processor are housed within the wearable device.

19. The non-invasive measurement system of claim 10, wherein:
    the array of SPAD detectors are further gated to:
        detect the light during a second capture period starting at a second time delay within each of the pulses, the second capture period temporally separated from the first capture period and shorter in duration than each pulse included in the sequence of pulses, and
        generate a second set of electronic signals representative of the light detected during the second capture period starting at the second time delay within each of the pulses; and
    the processor is further configured to generate, based on the second set of electronic signals, a second sequence of speckle pattern image frames corresponding to the second time delay.

20. The non-invasive measurement system of claim 10, further comprising a light source configured to generate the sequence of pulses of coherent light.

* * * * *